United States Patent [19]

Ash

[11] 4,348,283

[45] Sep. 7, 1982

[54] RECIPROCATING DIALYZER HAVING SPACERS

[75] Inventor: Stephen R. Ash, Lafayette, Ind.

[73] Assignee: Purdue Research Foundation, West Lafayette, Ind.

[21] Appl. No.: 204,342

[22] Filed: Nov. 5, 1980

[51] Int. Cl.³ .............................................. B01D 31/00
[52] U.S. Cl. .................................. 210/321.3; 210/356
[58] Field of Search ...................... 210/356, 321.3, 648, 210/347

[56] References Cited

U.S. PATENT DOCUMENTS

| | | | |
|---|---|---|---|
| 3,362,540 | 1/1968 | Bluemle, Jr. ...................... | 210/321.3 |
| 3,411,630 | 11/1968 | Alwall et al. ...................... | 210/321.3 |
| 3,412,865 | 11/1968 | Lontz et al. ...................... | 210/321.3 |
| 4,071,444 | 1/1978 | Ash et al. ...................... | 210/648 X |
| 4,132,649 | 1/1979 | Croopnick et al. ................. | 210/347 |

Primary Examiner—Frank A. Spear, Jr.
Attorney, Agent, or Firm—John R. Nesbitt; Robert E. Harris

[57] ABSTRACT

A reciprocating dialyzer is described for use as an artificial kidney or other extracorporeal mass transfer device. A dialyzer unit includes a membrane package having an aligned pair of thin semi-permeable membranes forming a chamber between the interior faces to receive fluid (such as blood) to be treated, and spacing elements in dialyzate chambers at the exterior faces of the membranes which contact the membrances and limit their expansion, while allowing chemical transfer to the dialyzate slurry. A plurality of such treatment units received between spaced plates comprises a dialyzer. Blood flow into and out of the membrane packages is through a central conduit, with free slurry being introduced and withdrawn from the dialyzate chamber at the periphery of each unit. The spacing elements are flexible and of plastic with molded, porous or mesh material modified to provide central and rim seals as well as membrane engaging faces designed to limit membrane displacement and cause formation of a thin blood column while not unduly masking the membrane surfaces and allowing slurry flow at all times including when the blood chamber is filled with blood. Certain spacing elements also allow emptying of blood from the dialyzer without need for positive pressure on the fluid outside the dialyzer.

19 Claims, 21 Drawing Figures

RECIPROCATING DIALYZER HAVING SPACERS

FIELD OF THE INVENTION

This invention is directed to a dialyzer apparatus for use as an extracorporeal mass transfer device or artificial kidney, and more particularly, is directed to a reciprocating dialyzer apparatus with membrane spacing elements to enhance operation of the unit.

BACKGROUND OF THE INVENTION

Dialysis apparati are well known, and it is likewise well known that an essential feature of such an apparatus is the dialyzer unit in which the blood to be treated is brought into contact with one face of a semi-permeable membrane while the other face is brought into contact with a dialysate.

Most dialyzers now known or utilized are of the so-called "flow-through" type wherein blood is introduced into the treatment area through one conduit and, after treatment, discharged from the unit through a separate conduit. For such apparatus, the blood is commonly withdrawn from the patient through an artery or arterialized vein with the treated blood being then pumped back into the patient through a vein.

More recently, a reciprocating dialyzer has been suggested wherein the blood is introduced into the blood treatment area and then discharged, after treatment, through the same conduit as utilized for introduction of the blood into the blood treatment area. Such a dialyzer is shown in U.S. Pat. No. 4,071,444, wherein the blood is introduced into the blood treatment area, formed by a pair of thin semi-permeable membranes, through a central opening with dialysate being introduced into the unit for membrane contact at the periphery of the unit.

An important advantage of the reciprocating dialyzer is that it may be used with a suspension of sorbent in the dialysate. The sorbent keeps the concentration of toxic substances low in the dialysate, and thereby facilitates mass transfer across the membranes, as described in U.S. patent application Ser. No. 104,016, filed by S. R. Ash on Dec. 17, 1979, and entitled "Dialysis Material and Method For Removing Uremic Substances In An Artificial Kidney." With the use of sorbent suspension, the need for a large volume of rapidly flowing dialysate is obviated, and a portable dialyzer becomes a reality. A disadvantage of the suspension, however, is that, as a thick slurry, it is difficult to maintain in a unidirectional flow pattern through small orifices. Therefore, special attention must be made to the orifices and flow channels of any spacers or membrane limiters in the reciprocating dialyzer.

SUMMARY OF THE INVENTION

This invention provides an improved dialyzer unit for extracorporeal treatment of biologic fluid, and, more particularly, provides an improvement for a reciprocating dialyzer with the unit having spacer elements which limit membrane displacement and cause formation of a thin column of fluid to be treated while not unduly masking the membrane surfaces and allowing flow of treatment material (which may be a sorbent suspension) next to to the membranes, including those times when the chamber is filled with blood as the fluid to be treated.

It is therefore an object of this invention to provide an improved dialyzer apparatus.

It is another object of this invention to provide an improved dialyzer apparatus of the reciprocating type.

It is still another object of this invention to provide an improved dialyzer unit having spacer elements.

It is yet another object of this invention to provide spacer elements for a dialyzer unit.

It is still another object of this invention to provide improved spacer elements for a dialyzer unit which can empty of fluid, by elastic recoil of the membranes, without need for positive pressure outside the membrane packages.

With these and other objects in view, which will become apparent to one skilled in the art as the description proceeds, this invention resides in the novel construction, combination, and arrangement of parts substantially as hereinafter described and more particularly defined by the appended claims, it being understood that such changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which.

DESCRIPTION OF THE INVENTION

Figure 1:
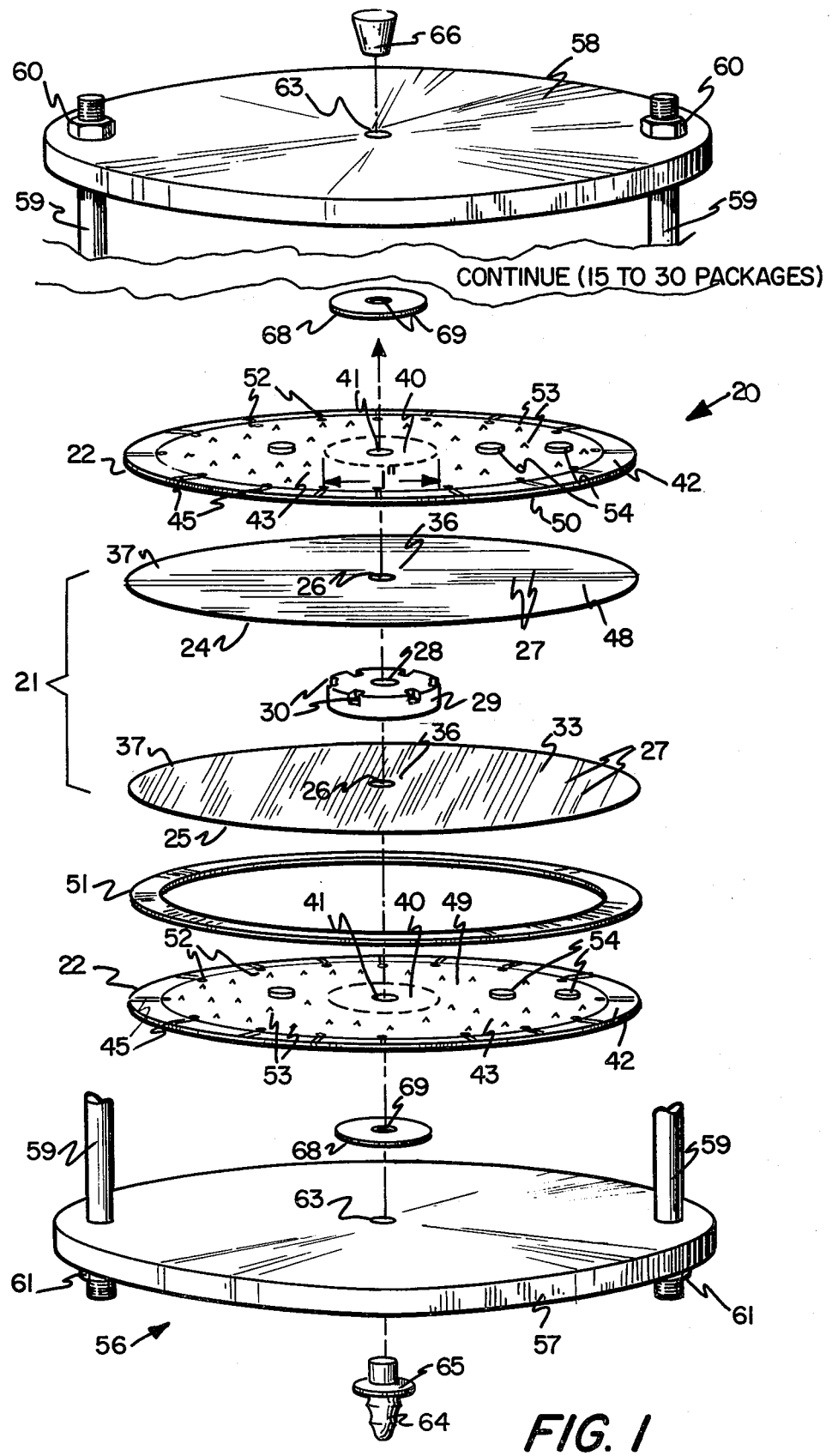
FIG. 1 is an exploded perspective view of the dialyzer apparatus of this invention positioned within a clamping unit.

Referring to the drawings, dialyzer unit 20 is shown in FIG. 1 to include a membrane package 21 with spacing elements 22 at the opposite sides thereof.

Membrane package 21 includes a pair of thin, semipermeable, disc-shaped membranes 24 and 25 that are coaxially positioned with respect to one another and each has a central aperture 26 therein with the apertures being aligned with one another. Each membrane has stress lines 27 therein and the stress lines of membrane 24 are oriented at an angle of 90° with respect to the stress lines of membrane 25 when in the operating position.

Figure 5:
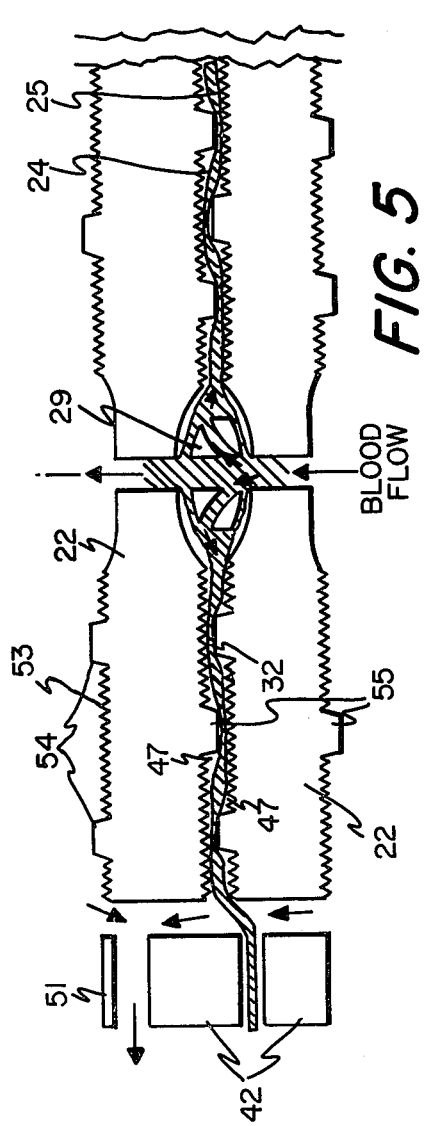
FIG. 5 is a partial side-sectional view of the dialyzer apparatus shown in FIG. 1 in the assembled position.

Central apertures 26 are also aligned with the central aperture 28 of a gasket 29 positioned between the membranes at the central portion thereof. As indicated in FIG. 1, gasket 29 has a plurality of notches, or slots, 30 which open the central aperture to the treatment area, or blood chamber (where blood is the fluid to be treated), 32 (as shown in FIG. 5) formed between the interior faces 33 of each of the membranes 24 and 25 when the membranes are sealed at the central, or hub, area 36 and at the periphery, or rim area, 37 as brought out more fully hereinafter. Attention is also directed to the reciprocating dialyzer shown in U.S. Pat. No. 4,071,444, which patent is hereby included by reference.

Spacing elements, or spacers, 22 are formed, as shown in FIGS. 1 through 5, by a flexible disc having a central portion 40 with a central aperture 41 therein, a rim portion 42, and a spacing, or membrane supporting, portion 43 extending between the central and rim portions. As shown in FIG. 1, spacers 22 are positioned coaxially with respect to membranes 24 and 25 and the central apertures 41 of the spacers are aligned with the central apertures of gasket 29 and membranes 24 and 25 so that a single central conduit is formed therethrough to chamber 32 formed between the membranes.

Figure 2:
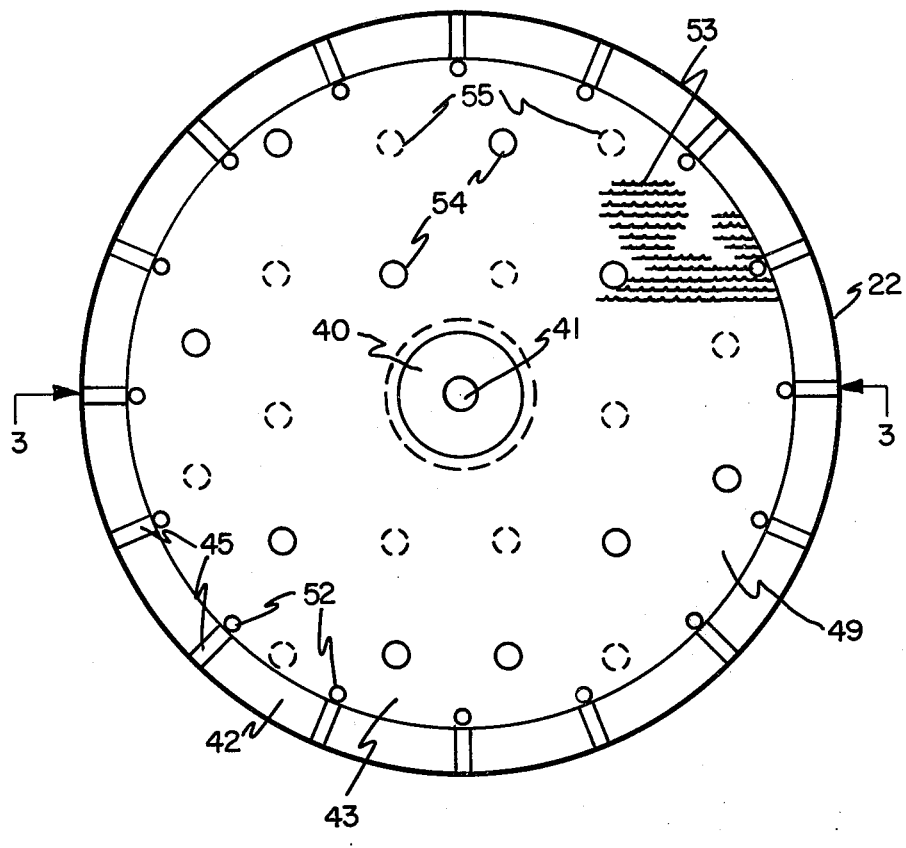
FIG. 2 is a top view of the spacing element shown in FIG. 1.

Central portion 40 and rim portion 42 of each spacer 22 is flat so as to provide central and rim sealing surfaces for the membranes. As shown in FIGS. 1 and 2, the rim portion 42 of each spacer 22 has a plurality of notches, or slots, 45 extending radially thereacross to provide a slurry inlet into the dialysis chamber 47 (as shown in FIG. 5) formed between the exterior face 48 of upper membrane 24 or lower membrane 25 (depending upon which is adjacent to the spacer) and the adjacent face of spacer 22 (i.e., the upper face 49 of the lower spacer 22 as shown in FIG. 1 and the lower face 50 of the upper spacer 22 as shown in FIG. 1).

As shown in FIG. 1, a ring 51 is preferably provided at the rim of each spacer 22 so that the notches are, in essence, ports leading from the outside of the unit into the dialysate chamber. While not shown, it is to be realized that the ring could be integrally formed with the rim portion with a passage therethrough forming the ports 45 through which the slurry can flow to and from the dialysate chamber. As also shown in FIGS. 1 and 2, an aperture 52 is provided adjacent to each slot 45 in rim portion 42 to allow slurry flow (i.e., flow of the treating solution which can be a suspension of sorbents for treatment of blood as brought out hereinafter between faces 49 and 50 of spacer 22.

Figure 3:
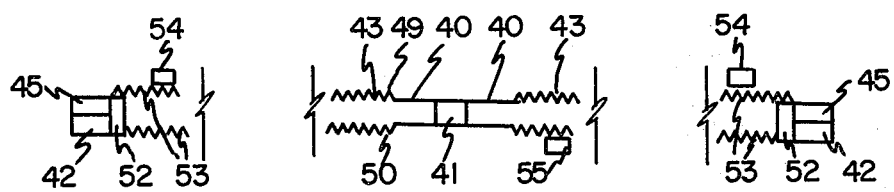
FIG. 3 is a partial cross-sectional view taken through the lines 3—3 of FIG. 2 and showing the protuberances of the spacing elements to have pyramid-like cross-sections.
Figure 4:
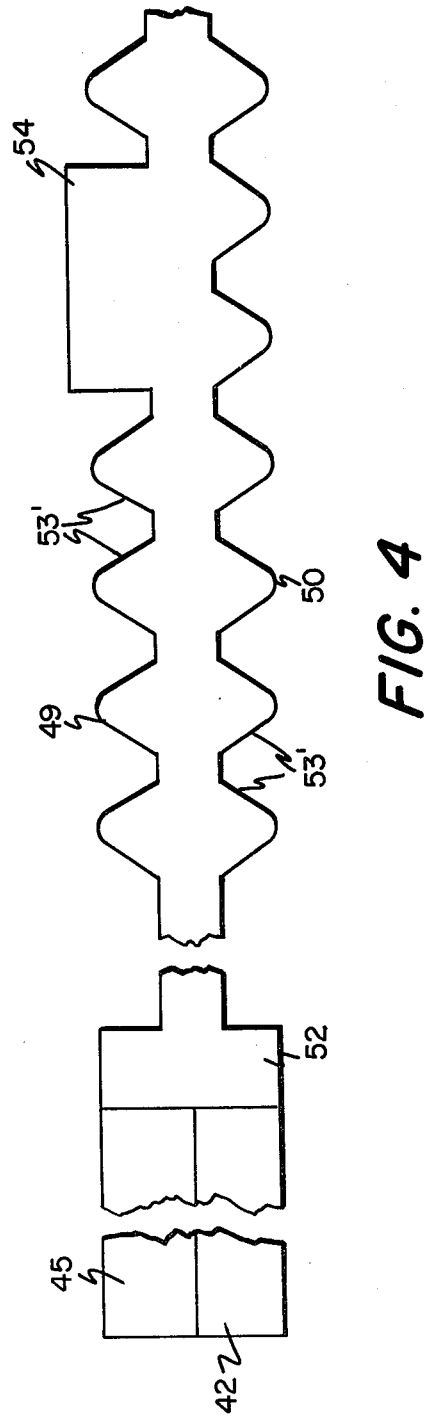
FIG. 4 is a partial cross-sectional view similar to that of FIG. 3 but showing the protuberances of the spacing elements having conical cross-sections.

The spacing, or middle, portion 43 of each spacing element 22 includes, as shown in FIGS. 1 through 5, a continuous series of protuberances 53 extending upwardly from a base pad (only a few of such protuberances being shown in FIG. 1 for illustrative purposes), it being realized that such protuberances are preferably closely spaced, uniform, and continuous as indicated by the broken area of FIG. 2 and in the cross-sectional views of FIGS. 3 through 5 so that the tops of the protuberances provide minimal membrane contact. As indicated in FIGS. 1 through 3, protuberances 53 may be a continuous series of protuberances having a pyramidal shape. As indicated in FIG. 4, however, the series of protuberances 53' may be a variety of tapered or pointed shapes, including a conical shape, and the conical shape is now preferred.

In addition, as also shown in FIGS. 1 through 5, a plurality of spaced columns 54 are fixed to the top face, or surface, 49 of each spacer 22, and a second plurality of columns 55, spaced from each other and spaced from lines extended normally through the spacer from columns 54 (as best shown in FIG. 2) are fixed to the bottom face, or surface, 50 of each spacer 22. As shown best in FIG. 5, columns 54 and 55 are in a square array to thus provide separate spaced column supports for stacking a plurality of membrane packages and spacers in the dialyzer apparatus, aligned as indicated in FIG. 1. As can also be appreciated, when the spacers are properly aligned by the support of columns 54 and 55, the protuberances act as limiters to limit the displacement of the membranes, and therefore limit the maximum volume of blood that can be introduced into the blood chamber.

Each dialyzer unit 20 is assembled for use in a positioning, or clamping, unit 56 consisting of a base plate 57 and top plate 58 having a plurality of rods, or bolts, 59 extending therethrough as shown best in FIG. 1. As indicated in FIG. 1, a plurality of units 20 are normally stacked on base plate 57 (a removable center post (not shown) can be utilized for alignment of the central apertures during stacking if desired). The plates are then compressed (as by tightening nuts 61 at the lower ends) to form and maintain the central and rim seals for each membrane package 21 (the seals being provided by the spacer elements 22 at each side of each membrane package as brought out hereinabove).

Plates 57 and 58 each have a central aperture 63 therein which aperatures are aligned with the apertures on the membrane package and spacers. A fitting 64 with a gasket 65 thereon is provided in aperture 63 of base plate 57, and blood (or other fluid to be treated such as peritoneal dialysis fluid) is introduced through this aperture and the central conduit into the blood chamber and then withdrawn through this same conduit and blood fitting from the chamber. A plug 66 is provided at the top plate 58 provided at the aperture 63 in top plate 58, and washer 68 with central aperture 69 therein are provided adjacent to the base and top plates to aid in sealing.

In a working embodiment of the dialyzer unit, shown in FIGS. 1 through 5, membranes 24 and 25 were cuprophan membranes (150 pm) having a five inch diameter with a 0.25 inch central aperture; blood gasket 29 was a 0.75 inch diameter disc of polyethylene material of 0.04 inch thickness with a 0.25 inch central aperture; spacing elements 22 were of polyethylene material having a five inch diameter with a central portion of one inch diameter and 0.02 inch thickness with a 0.25 inch diameter central aperture and a rim portion having a 0.25 inch diameter and 0.02 inch thickness; ring 51 was of polyethylene material having a 4.75 inch interior diameter and 5 inch outside diameter and a thickness of 0.02 inches; gaskets 68 were 0.75 inch diameter discs of silicone rubber of 0.02 inch thickness with a 0.25 inch diameter central aperture; base and top plates 57 and 58 were aluminum plates having a 6.375 inch diameter with a 0.25 inch thickness and a 0.25 inch diameter central aperture, with each plate having six spaced apertures at the rim to receive 5/32 inch diameter rods therethrough of a length of 4 inches to 8 inches; protuberances 53 of pyramidal-shaped cross-section had tops extending 0.012 inches from the surface to the outwardly extending tops, or tips, of the pyramids with a pyramid density of 25 per inch in a square array on each side of the spacer; cones 53' (as shown in FIG. 4) each had a 0.031 inch base with a separation at the base between cones of 0.008 inches and a cone height of 0.02 inches with a distance between cone tips of 0.04 inches, and with each cone sidewall forming a 33.7° angle with respect to a line normal to the spacer surface with the top of each cone having a 0.006 inch radius; columns 55 and 56 were of polyethylene material having a ⅛ inch diameter and 0.01 inch thickness; notches 45 had a width of 1/16 inch and a depth of 0.02 inches with apertures 52 being of 3/32 inch diameter. The foregoing is meant to be illustrative of a working embodiment of the unit and the invention is not meant to be limited thereto. The elements of the unit could, for example, be square or rectangular, rather than round, could be of different dimensions or characteristics, as, for example, being of seven inch diameter or the membranes being more permeable (100 pm, for example), of different materials, having a different configuration of protuberances and/or columns, and/or have a different number of notches 45, such as, for example, 32 notches, all of which would be obvious to one skilled in the art.

Figure 6:
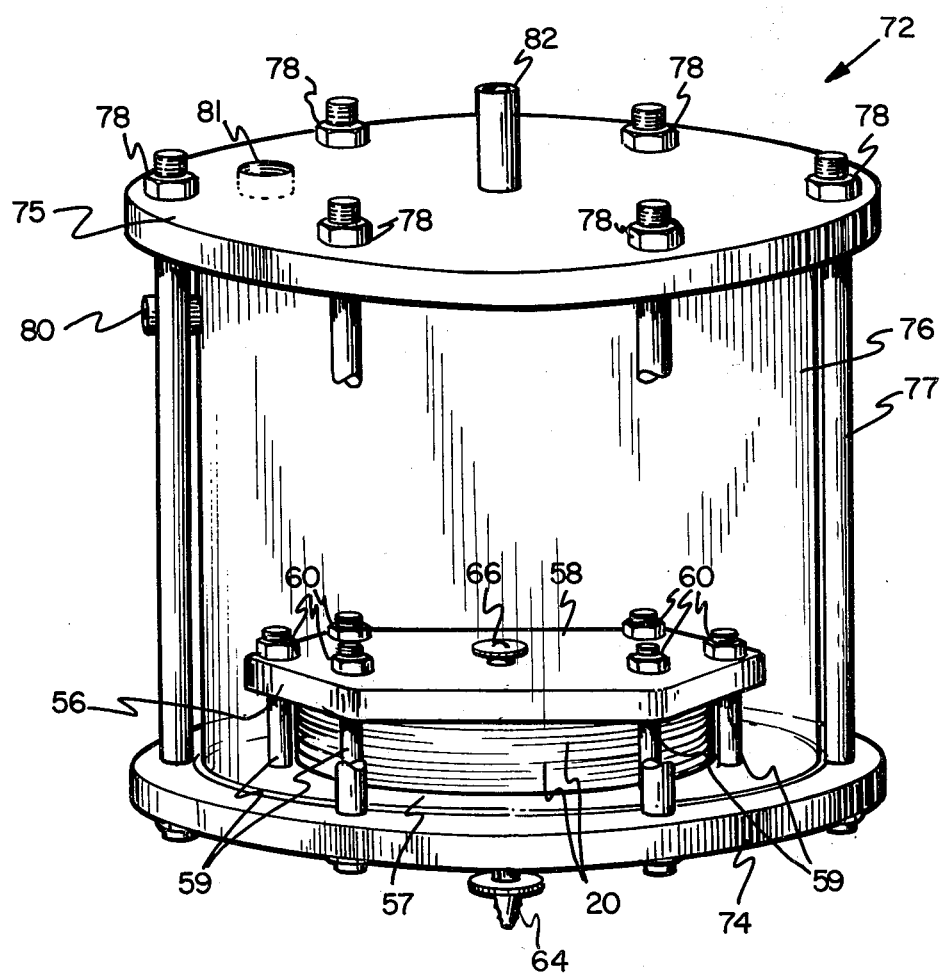
FIG. 6 is a perspective view of a case unit for housing dialyzer units with a plurality of membrane packages.

A plurality of membrane packages are normally stacked in a clamping unit 56 having base and top plates 57 and 58 (which are shown to be of hexagonal shape but can be circular if desired), as brought out hereinabove. This assemblage is then placed, for use in a reciprocal dialyzer apparatus, in a case assembly 72 as shown in FIG. 6. As shown, case 72 includes a bottom plate 74 (which can be combined with base plate 57), a top plate 75 and cylindrical sidewalls 76, with the unit held to form a sealed enclosure by means of a plurality (six as shown) of rods, or bolts, 77 having nuts 78 thereon (with sealing gaskets being used as needed). This configuration can also be varied as desired for a particular use.

Bottom plate 74 has blood fitting 64 extending therethrough and slurry port 80 is formed in sidewall 76. Top wall 75 also has a threaded fill hole 81 and a vent 82 (which is used to expel air from case assembly 72 and then is closed). The slurry is inserted into, and sealed within, the air-tight case 72 with slurry preferably entirely filling the case so that no air remains. The slurry is then used to pump the membrane packages (by use of a slurry pump (not shown) so that the blood moves passively as a result of increased and decreased slurry pressures (to cause slurry compression and decompression).

Figure 7:
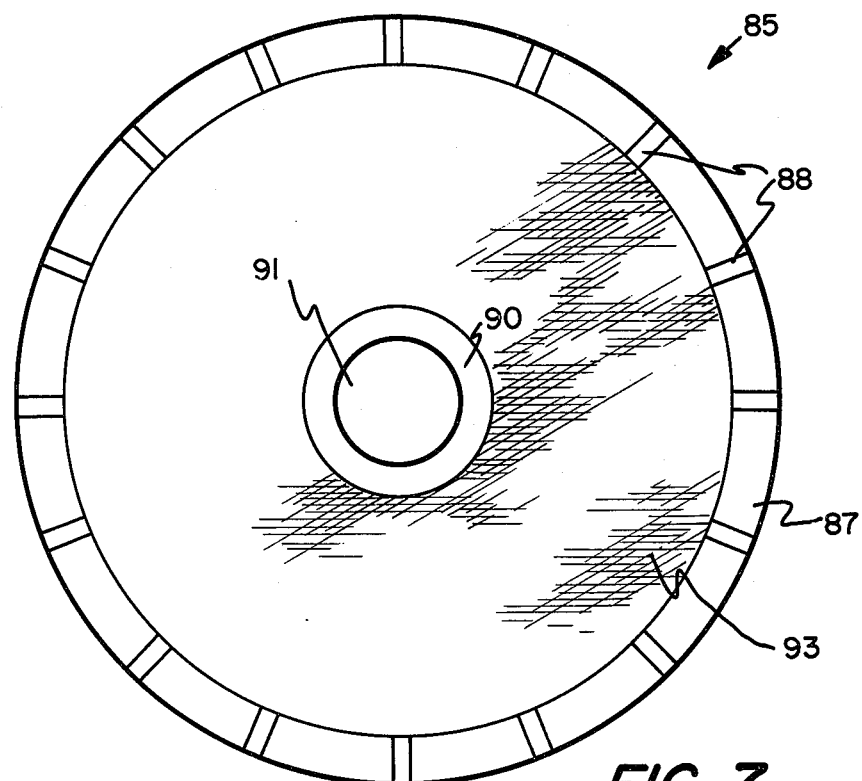
FIG. 7 is a top view of an alternate embodiment of a spacer element of mesh construction.
Figure 8:
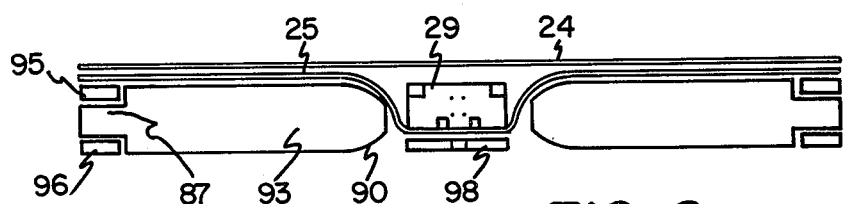
FIG. 8 is a partial exploded side-sectional view of a dialyzer unit using the spacer element as shown in FIG. 7.
Figure 9:
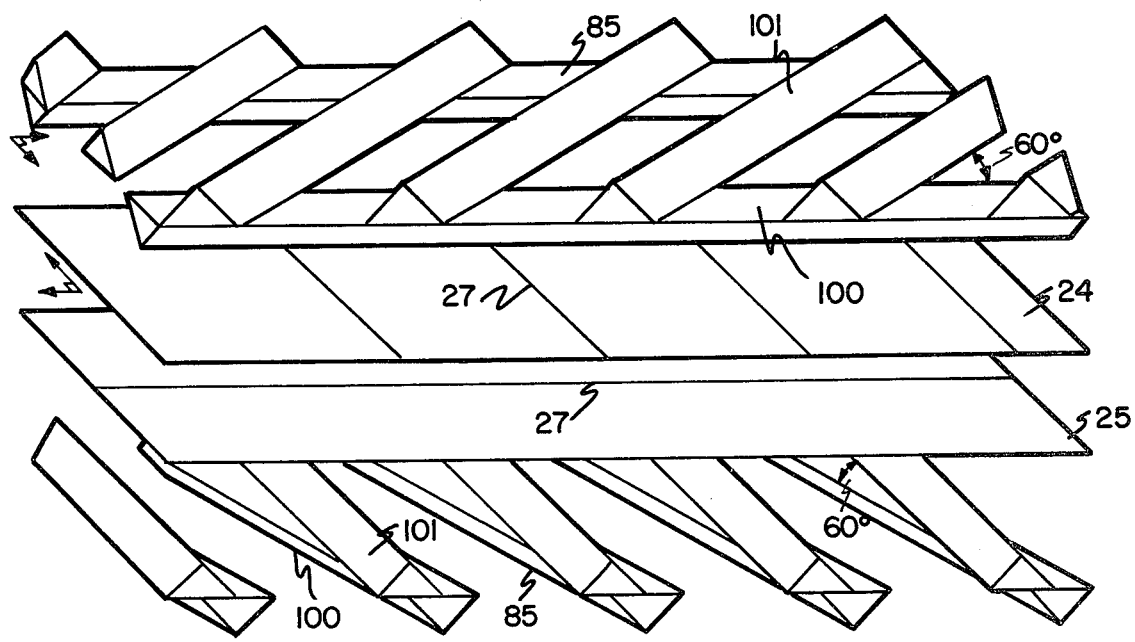
FIG. 9 is a partial illustrative presentation of screen contact with the membranes for operation of a dialyzer unit as shown in FIGS. 7 and 8.

An alternate embodiment 85 of the spacer element is shown in FIGS. 7 through 9. As shown in FIG. 7, spacer element 85 is similar to spacer element 22 in providing a solid and flat outer rim portion 87 having a 0.02 inch diameter and a solid central portion 90, except that the solid central portion is of diminished size and terminates in a one inch diameter aperture 91. The central and rim portions are preferably melted by application of heat to form the solid and substantially flat portions thereat.

The membrane-engaging portion 93 between the central and rim portions of spacer 85 is of mesh or woven construction and preferably is a screen.

An exploded side-sectional view of the dialyzer unit when utilizing spacer elements 85 is shown in FIG. 8. As shown, a pair of rings 95 and 96 are positioned at opposite sides of the rim portions 87 of the spacer element 85 (notches 8, as shown in FIG. 7, provide and input for slurry) and membranes 24 and 25 are positioned adjacent to the spacer element 85 (only one set is shown in FIG. 8) with blood gasket 29 therebetween in the same manner as described hereinabove with respect to blood treatment unit 20, except that an added central washer 98 is preferably utilized. A second spacer element 85 (not shown in FIG. 8) is positioned at the other side of each membrane package to thus seal the membranes between the spacer elements and thus to establish the blood chamber between the membranes and the dialysis chambers outside the membrane package in the same manner as described hereinabove with respect to blood treatment unit 20.

An exploded representation of membrane contact with screen 85 is shown in FIG. 9. As shown, screen 85 includes strands 100 and 101 oriented at 60° angles with respect to one another with strands 100 of screen 85 (of the top spacer element) contacting the top membrane 24 at an angle of 90° with respect to the stress lines of membrane 24, and with strands 101 of screen 85 (of the lower spacer element) contacting the lower membrane 25 also at an angle of 90° with respect to the stress lines of membrane 25 (the stress lines 27 of membranes 24 and 25 are oriented with stress lines at an angle of 90° with respect to one another).

The screen spacer element 85 allows the dialyzer unit to exert negative pressure on the dialysate side throughout the pumping cycle. The blood volume in the blood chamber is nearly zero until a vacuum is pulled on the slurry to open the membranes into the screen voids. When the vacuum is then released, the elastic recoil of the membrane creates enough pressure to force all or most of the blood out of the blood chamber formed by the membrane package. A uniform, thin blood column is also provided by use of screen spacer element 85 and this element also allows a denser slurry suspension to be utilized (up to 500 grams of solids per liter of liquid which constitutes nearly a 100% reduction in water mass and slurry volume), allows the overall flow requirements of the dialyzer apparatus to be reduced, and can reduce an ammonia problem by better mixing of the slurry.

In a working embodiment of the blood treatment unit utilizing spacer elements 85, the elements utilized for blood treatment unit 20 were utilized except that spacer element 85 of polyethylene having a thickness of 0.05 inches at the screen portion 92 and 0.02 inches at the flat rim portion 87 was utilized in lieu of spacer element 22, a 0.75 inch diameter washer 98 of cellulose acetate with a 0.01 inch thickness and a 0.25 inch diameter central aperture was utilized, and rings 95 and 96 of polyethylene with a thickness of 0.015 inches were utilized in lieu of ring 51 as used in spacer element 22. Here again, this is meant to be illustrative of a particular embodiment and the invention is not meant to be limited thereto.

The blood treatment unit of this invention thus provides a free-sorbent dialyzer which utilizes spacer elements providing membrane supports that create thin packages for blood flow in the blood chamber. By providing protuberances on the membrane engaging portions of the spacer elements, minimal contact is made by the spacer elements with the membranes to thus avoid undue masking of the membrane surfaces and yet permits slurry flow at all times including when the blood chamber is filled with blood.

The dialyzer apparatus uses a sorbent suspension having free access from a reservoir to the spaces between the membrane packages. At a treatment rate of 150 ml/min-$M^2$, the in vitro creatinine clearance has been found to be 75 ml/min-$M^2$. The creatinine clearance, flow resistance, and compliance of the dialyzer have also been found to be constant during four to six hours of test. In vivo tests have shown that during urea and creatinine infusion in a normal dog and in a dog with ¾ nephrectomy, the in vivo creatinine clearance agrees (within ±10%) with the in vitro clearance. Sodium, potassium, calcium, and bicarbonate fluxes have been found to be within limits acceptable for patients in renal failure. The blood treatment unit of this invention allows higher clearance for urea and creatinine, and larger amounts of sorbent to be used, with construction and sterilization being simplified so that this invention allows the dialyzer apparatus to be a portable, single-needle, self-contained, solo-operated artificial kidney.

The dialyzer unit of this invention is preferably used with a slurry that includes absorbent chemicals, to regenerate dialysate. This sorbent suspension is described in U.S. Pat. application Ser. No. 104,016, filed by S. R. Ash on Dec. 17, 1979, and entitled "Dialysis Material and Method for Removing Uremic Substances In An Artificial Kidney." Preferably, a high sorbent suspension concentration is provided, such as a suspension of about 27 wt% of sorbent such as activated charcoal, calcium-sodium loaded zeolites, and/or urease, which is introduced into the dialysate chambers as the treating solution. A reciprocating flow of blood to and from the blood chamber formed by the membrane packages was effeced by modest pressure changes in the sorbent suspension (−200 to +100 mm Hg) and this helped mix the sorbent suspension. Chemical efficiencies can result that are approximately as high as achieved with flow-through dialyzers when the sorbents in the dialysate are well mixed and the dialysate concentration of uremic substances is kept low, the membrane packages are emptied completely during each cycle, and the mass transfer remains constant during filling and emptying of the membrane packages or the dialyzer is operated at a trapezoid mode, in which the time of filling and emptying is only a small fraction of the total cycle time. Thus, the creatinine clearance/$M^2$ of a reciprocating dialyzer is nearly equal to that of flow-through dialyzers, with a blood column thickness of approximately 400 μm, and a cycle time of approximately 60 sec.

In vitro and in vivo tests of the function of such a constrained suspension reciprocating dialyzer showed that the sorbents were minimally saturated, and thus relatively well mixed, during use. Dialysis of up to nine hours could be achieved with little decrease in mass transfer coefficient. In this invention, the sorbent suspension is allowed free access between the case assembly enclosing the blood treatment units and the dialysate spaces, or chambers, between the membrane packages. In addition, the entire apparatus can be assembled and sterilized in the absence of a sorbent suspension, and can be utilized with as large a suspension volume as needed to prevent saturation.

Through testing of the flow of the sorbent suspension through a flow pattern typical of a blood treatment unit such as shown in FIGS. 1 through 5, it was found that the volume of slurry flow per cycle into each membrane package should be considerably less than 10 ml, that the length of time of rapid flow should be considerably less than 30 seconds, and that minimal protein binding should be utilized (20 mg/gm zeolite with specific activity adjusted to yield 20 IU/ml in the final suspension). Each dialyzer unit of this invention was thus designed with an expected fill volume of three to four ml per membrane package with unimpeded flow of the sorbent suspension between the membrane and the support (during membrane package expansion and collapse), a thin, uniform blood column thickness, at full expansion of the membrane package, and minimal masking of the membrane (i.e., contact with the membrane supports) to provide continued transfer of solutes from the blood side to sorbent suspension at full membrane expansion.

Figure 10:
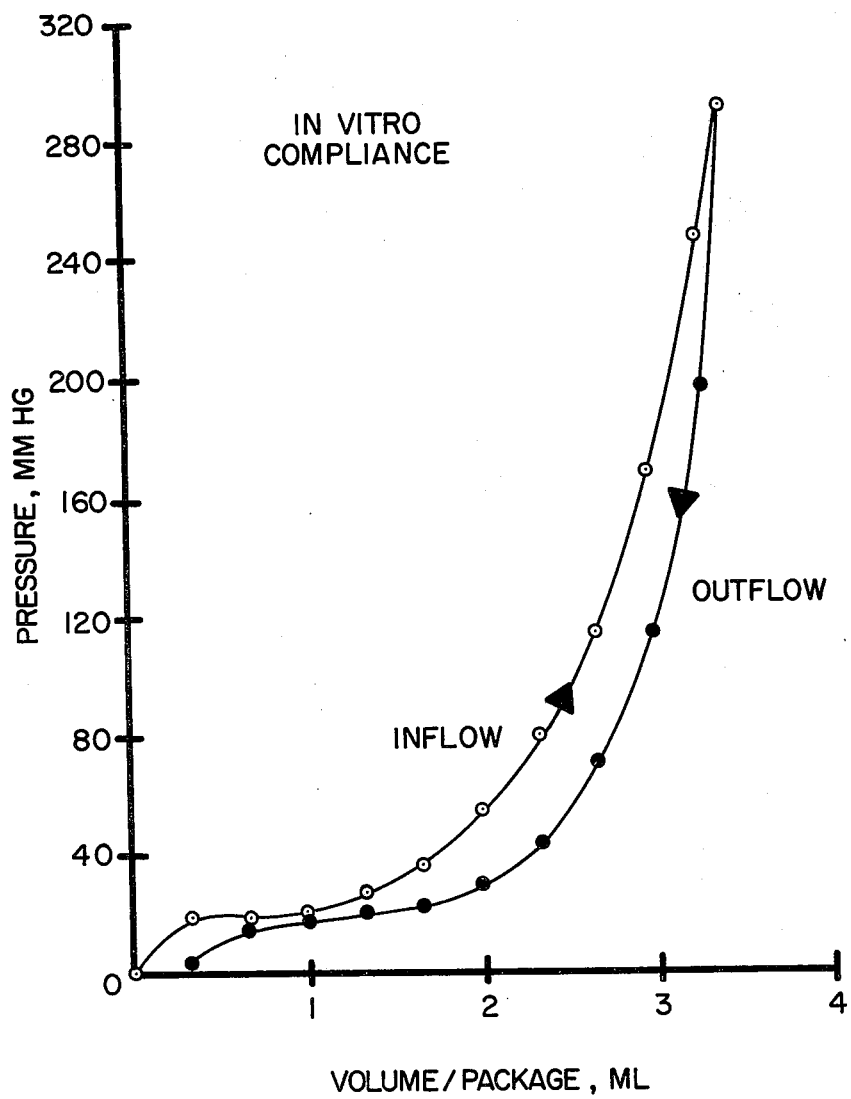
FIG. 10 is a graph showing a typical in vitro compliance curve for a dialyzer apparatus as described herein.

A dialyzer apparatus having dialyzer units 20 (as shown in FIGS. 1 through 5) encased in case assembly 72 (as shown in FIG. 6) was subjected to hydraulic tests. After air testing of the apparatus and filling the dialyzer with saline, a three-way stop cock was attached to the blood inlet port of the dialyzer and a mercury manometer was then attached to one port of the stop cock. With a 60 milliliter syringe, saline was injected into the dialyzer and pressure recorded up to 300 mmHg. A typical volume versus pressure (compliance) curve is shown in FIG. 10. In repeated trials, 3.5±0.7 ml per membrane package could be injected before the pressure reached 300 mmHg. The compliance curve for outflow was similar to inflow, if small corrections for ultrafiltration and trapped volume are taken into account. This indicated that work performed in filling could be partially recovered in emptying of the packages.

Figure 11:
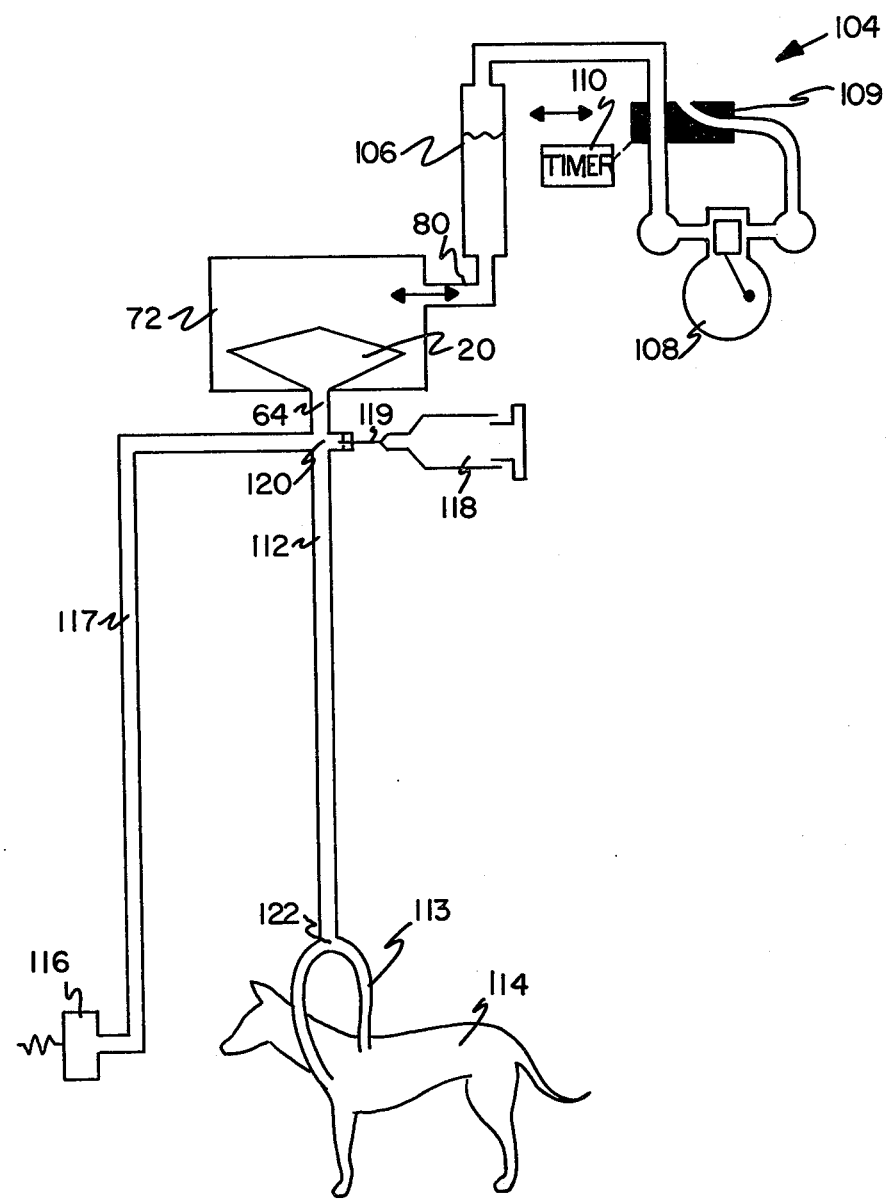
FIG. 11 illustrates a test set-up for testing of the dialyzer apparatus.

Alterations in pressure of the sorbent suspension was used to promote movement of blood into and out of the dialyzer apparatus, without need for a blood pump. A pressure-vacuum system 104 was used to change dialysate pressure during in vivo tests, as illustrated in FIG. 11. As shown, a 250 ml graduated reservoir 106 was provided with the lower end in communication with port 80 of case assembly 72 having membrane packages 20 therein. The air-fluid level of reservoir 106 was approximately 40 cm above the blood inlet point provided at blood fitting 64.

A pressure pump (0.5 H.P.) 108 generated positive and negative pressures ranging from −200 to +100 mm mercury in reservoir 106. An electric valve 109 actuated by a timer 110 controlled the cycling of positive and negative pressure with cycle times of 60 to 120 seconds being produced, with inflow-outflow ratios of approximately 3:1. The blood inlet 64 was attached to a silicone tube (⅜ inch I.D.) 112 and the tube was attached to an arterio-venous shunt 113 of the test animal 114. In addition, pressure gauge 116 was connected in communication with tube 112 through tube 117, and samples were injected into tube 112 by means of sample syringe 118 and needle 119 at three-way connector 120. Total volume of fluid within the case and reservoir was determined by following the location of the air-fluid interface in the 250 ml reservoir 106. Volume changes in case 72 were assumed to be due to (1) blood flow into or out of the dialyzer, (2) ultrafiltration of fluid into the dialyzer, and (3) case compliance, a 20-30 cc volume change occurring rapidly after pressure change, in the absence of blood flow into the dialyzer.

Calculation of inflow and outflow resistance of the dialyzer was based on the assumption that the flow rate into the dialyzer would be proportional to the difference between the hydrostatic pressure head, $P_H$, and the pressure due to compliance of the membranes, $P_c$. According to this assumption, flow into the dialyzer could be described as follows:

$$\text{Blood flow rate} = \frac{dV}{dT} = Q = \frac{P_H - P_c}{R} \quad (1)$$

where $P_c$ = back pressure due to compliance of membranes, a function of volume in the membrane package,
$P_H$ = pressure head during resistance tests (+ for gradient from blood access to dialysate), and
$R$ = overall resistance of dialyzer and inlet tubing
Equation 1 is difficult to solve exactly, due to the complex relationship of $P_c$ to V. However, it is possible to obtain a numerical approximation:

$$\sum_{1}^{n} \frac{\Delta V_i}{P_H - P_{ci}} = \frac{1}{R} \sum_{1}^{n} \Delta t_i = \frac{t}{R} \quad (2)$$

The n data points obtained during blood flow tests can thus be analyzed utilizing data from the compliance tests, and graphically represented as:

$$\Sigma \frac{\Delta V_i}{P_H - P_{ci}} \text{ versus } t$$

The resistance of the dialyzer may then be determined from the slope of this graph.

An in vitro fractional removal mass transfer test was designed to determine the efficiency of mass transfer of a reciprocating dialyzer at simple operating modes over a wide range of cycle times. Changes in concentration between inflow and outflow fluid were used to indicate chemical efficiency. Fill volumes were chosen for each dialyzer which would produce less than 300 mmHg pressure as determined by the compliance test. A simplified sorbent suspension was utilized, containing charcoal (7 wt%) and methocel (½%) but omitting zeolite and urease. A solution of 100 mg% urea, 20 mg% urea, 20 mg% creatinine was prepared in 0.7 to 0.9% saline. Syringes 118 were filled to the appropriate volume with this fluid at room temperature. The fluid was injected in the following two flow modes into the membrane package through the blood inlet port: (1) the "trapezoid" mode, in which the fluid was injected as rapidly as possible (within 5 seconds), maintained at a constant volume, and withdrawn as rapidly as possible (about 10 seconds), and (2) the "saw-tooth" mode, in which the dialyzer was filled and emptied at constant volumetric low rate and with equal inflow and outflow time segments.

The entire effluent was collected from each cycle, mixed, and the creatinine and urea concentration measured. A Beckman automatic creatinine analyzer (Jafee method) was used for creatinine and urea assays. Cycle times of 30, 60, 120, and 240 seconds were tested. The overall-mass-transfer coefficient ($K_o$) for a certain cycle time was calculated according to the following formula:

$$K_o = \left( \ln \frac{C_i}{C} \right) \frac{V_f}{A\tau} \quad (3)$$

where C and $C_i$ are the average effluent and influent concentrations, respectively, A is membrane area, and $\tau$ is cycle time. In theory for a given dialyzer and solute tested, $K_o$ should depend not only on the mode of injection (trapezoid or saw-tooth), and fill volume $V_f$, but also on cycle time, (due to the effect of first order diffusion through numerous stagnant blood-side layers). Since the dialyzer is expected to be operated at 50% creatinine removal, however, it is helpful to calculate an overall mass-transfer coefficient $K_{o,0.5}$ which yields 50% efficiency at a certain cycle time $\tau$. From substitution in Equation 3, $K_{o,0.5}$ may be calculated by $$K_{o,0.5} = (\ln 0.5) \frac{V_f}{A\tau} = 0.693 \frac{Q}{A} \quad (4)$$

where Q = volume of blood treated per unit time. Given $K_{o,0.5}$ from in vitro tests, a desired treatment rate of a dialyzer (e.g., 200 ml/min), and the desired efficiency (50%, or a clearance of 100 ml/min), the above equation predicts the total membrane area required for a given design.

For tests of dialyzer efficacy, the best model is, for this reason, an animal with a high urea and creatinine concentration. An animal model was created with renal insufficency and with a high urea/creatinine load. Renal insufficiency was achieved by total removal of one kidney and ligation of one of two arteries to the other kidney.

A healthy mongrel dog 114 weighing 26 kilograms was anesthetized using sodium phenobarbital. The dog was maintained under anesthesia with nitrous oxide and fluothane. The neck area was thoroughly prepped and shaved. A two inch long vertical incision was then made over the carotid sheath area. An arterio-venous shunt 113 was fabricated from ⅛ inch I.D. silicone rubber tubing (Silastic[R], Dow Corning, Midland, Michigan) and straight teflon connectors (Quinton Instrument Company, Seattle, Wash.). On the outside of the silicone rubber tubing, at a point which would come to lie just underneath the skin exit site, a cuff made of Dacron velour (Vicra Company) was glued to the tubing with Silastic adhesive type B. Fibrous ingrowth into this Dacron velour served a dual purpose of immobilization of the catheter and prevention of bacterial growth along the catheter tract. Teflon connectors were placed in the arterial and venous portions of the shunt, inserted into the carotid artery and jugular vein, and tied in place. The tubing was tunneled to the back of the neck, and a skin exit site made just distal to the Dacron cuff. The arterial and venous cannulae were brought through the skin and connected with a Teflon straight connector. Blood flow was observed. The catheter was then bandaged to the neck and protected with a neck collar made of 0.040 inch polyethylene.

After construction of the arterio-venous shunt, the dog was placed with spine downward, and the abdomen thoroughly prepped and shaved. A midline incision was made about five inches long. The right and left kidney were then isolated. A previous arteriogram indicated that two renal artery branches were present to the right kidney, and this was confirmed during surgery. The arterial branch was ligated. A left nephrectomy was then performed after pedicle ligation. The abdomen was then closed by layers, and the animal allowed to recover. Following surgery the animal was placed on 250 mg ampicillin orally, twice daily. Keflin 250 milligrams was given IV at the end of each dialysis. Anticoagulation was achieved with Ascriptin (each tablet containing 325 milligrams of acetylsalicylic acid plus magnesium and aluminum oxide). Heparin, 2,000 to 3,000 units, was administered intravenously every eight hours, if there was evidence of clotting of shunt.

The blood urea nitrogen and creatinine were measured daily for one week, and then approximately three times weekly after that. The BUN rose to 60 mg% and creatinine to approximately 3.5 mg%, at which point they both stabilized.

It was found that BUN and creatinine slowly return towards normal following this "$\frac{3}{4}$" nephrectomy. If BUN were less than 30 and creatinine less than three, in order to produce a more realistic model of uremic chemistries, a urea creatinine infusion was utilized. This infusion was performed through the intestinal route, to avoid need for sterilizing the solution, and to simplify infusion. A nasogastric tube was placed into the animal's stomach and one liter of water injected containing 35 gm urea, four gm creatinine solution. Following this, BUN was found to rise to at least 50 and creatinine to rise to at least six, in the $\frac{3}{4}$ nephrectomized animal. Urea level stayed above 40 even during the dialysis procedure. No signs of toxicity were seen following infusion.

The blood compartment was sterilized with Betadine (PVP-iodine). The membrane package was filled with Betadine, left for 10 minutes, then removed by syringe. After this, several syringes of saline (sterile irrigation fluid) were injected and withdrawn fom the dialyzer apparatus. The process was continued until the iodine color (light yellow) nearly disappeared. After placing the sorbent suspension in the case, several cycles of the fluid resulted in complete removal of the light yellow color. The dialyzer apparatus was then attached to the shunt of the dog, using $\frac{1}{8}$ inch I.D. silicone tubing 112 and a three-way connector 122. Blood flow into and out of the dialyzer apparatus was promoted by changes in pressure in the sorbent suspension. The cycle time of pressure-vacuum was controlled by timer 110 and air valve 109. The air-fluid level in the reservoir was 40 cm higher than the heart of the animal. Four-way connector 120 was placed within the $\frac{1}{8}$ inch I.D. silicone tube, connecting the shunt with the dialyzer. A rubber cap was attached to one of the ports of this four-way connector for drawing inflow and outflow blood samples with a penetrating needle and syringe. On the opposite side of the four-way connector, a tube was connected to a pressure transducer. This pressure transducer was placed at the level of the animal's heart. Pressure was recorded versus time on a Physiograph 4 channel recorder. Volume changes of fluid in the case were recorded by visual observation of the air-fluid interface in the reservoir. The volume changes were confirmed during sampling of the total outflow of the dialyzer, as described below. Fluid accumulation caused by ultrafiltration was removed from the reservoir using a syringe and catheter.

Activated clotting time (Vacutainer, Becton Dickson) was used to indicate the animal's need for heparin during dialysis. Measurement of activated clotting time was repeated every half hour. The initial activated clotting time of the dog was approximately two minutes. Experience in dialysis both with the reciprocating dialyzer and standard hollow fiber dialyzers indicated that 3.5 to four minutes activated clotting time was necessary to insure lack of coagulation. Either 1,000 to 2,000 units of heparin was injected into the animal depending on whether the activated clotting time was one or two minutes away from this goal. Arterial blood pressure was recorded with the Physiograph when the venous portion of the shunt and the inlet to the dialyzer were clamped. During dialysis, the pressure transients occurred during inflow and outflow. These transients were useful in confirming flow into and out of the dialyzer apparatus. Any obstruction to flow within the dialyzer apparatus caused a lessening of pressure changes. An inlet obstruction at the shunt or venous cannala caused an accentuation of pressure changes.

Once evey half hour, inflow and outflow blood samples were drawn for chemical analysis. For inflow samples, the timer was stopped at the end of inflow and a clamp placed between the four-way connector and the dialyzer case. A sample of blood was removed using a needle and syringe at four-way connector 120. This sample was mixed, and the serum immediately separated. Outflow samples were obtained by clamping the tube between the four-way connector and the shunt. The dialyzer was then placed on a pressurized (outflow) cycle and all outflowing blood was removed using a syringe or sterile, vinyl bag. This blood sample was measured, mixed well, and a portion removed for immediate preparation of serum. The remainder of the sample was then re-injected into the shunt. Chemical analyses of serum included calcium, sodium, potassium, pH, $pCO_2$, creatinine, and BUN, for both inflow and outflow samples. Plasma ammonium for inflow and outflow samples was determined by the $\alpha$-ketoglutarate method (Sigma). Creatinine and urea were determined by Beckman automatic analyzers (Jafee and Berthelot methods). Base excess was calculated from pH and $pCO_2$, using the Henderson-Hasselbalch equation and blood titration curves.

Figure 12B:
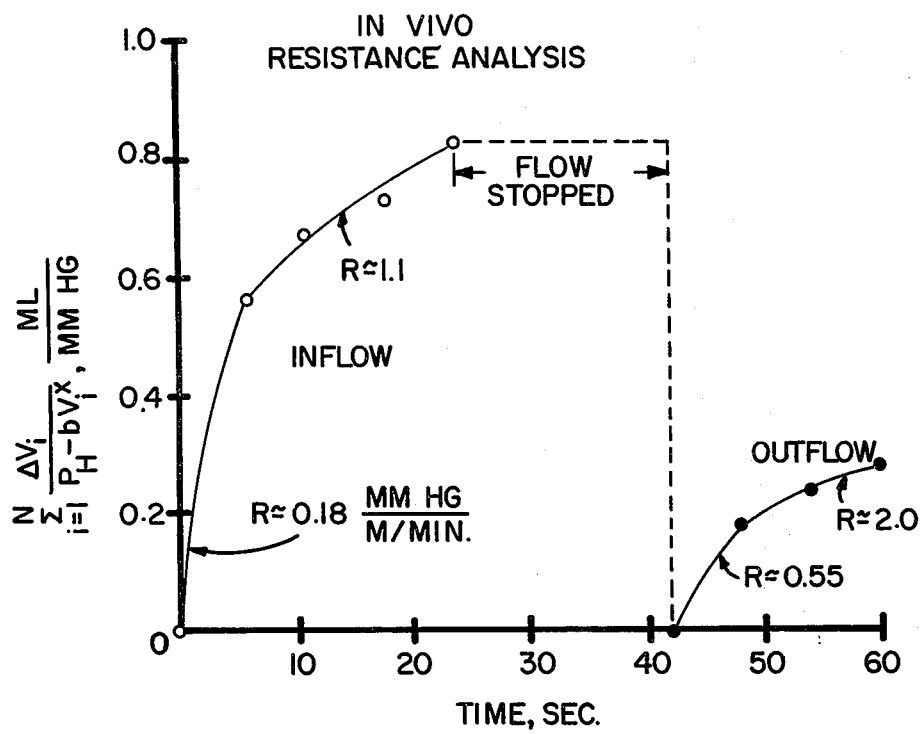
FIG. 12(b) is a graph illustrating in vivo resistance analysis of flow depicted in FIG. 12(a) and encountered during testing of the dialyzer apparatus.
Figure 12A:
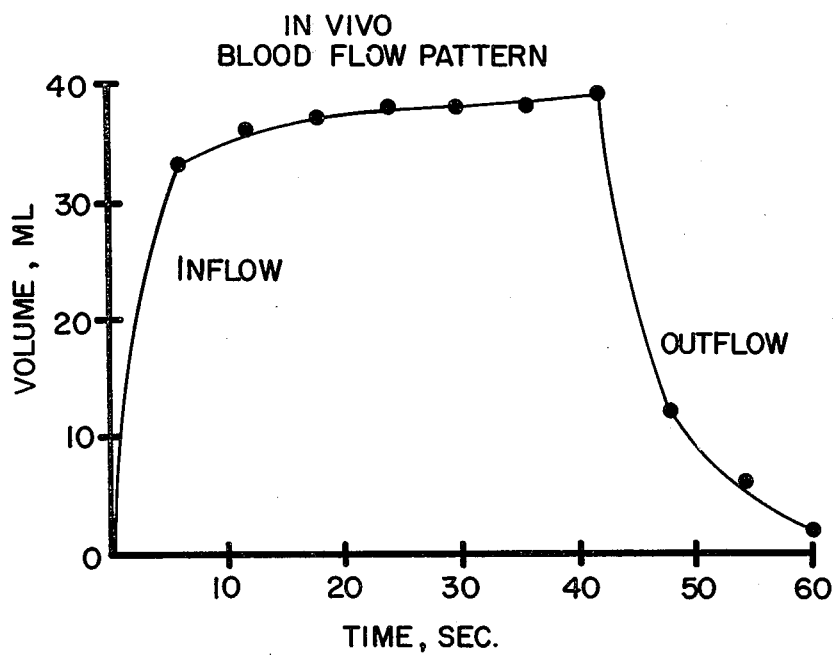
FIG. 12(a) is a graph showing dialysate volume in the reservoir during in vivo testing of the dialyzer apparatus with the apparatus shown in FIG. 11.

FIG. 12($a$) shows the dialysate volume in the reservoir (representing blood volume) during in vivo testing of a 15 package modified pyramidal support dialyzer. Case pressures were $-200$ mm Hg for inflow (42 seconds) and $+100$ mm Hg positive pressure for outflow (18 seconds). Flow rate is initially rapid and slows down asymptotically, as flow is limited by compliance of the dialyzer. During outflow, flow is initially rapid, but gradually diminishes. Ultrafiltration is negligble within any one cycle. Changes of dialysate volume in the reservoir are, thus, due to blood flow into and out of the dialyzer and case compliance. Case compliance, a 20–30 cc, occurs immediately on pressure change and is subtracted from all subsequent reservoir-dialysate readings to yield changes of blood volume in the dialyzer. A constant hydrostatic pressure head, $P_H$, is present during inflow and during outflow. This pressure head is calculated using the mean shunt pressure, air pressure of the reservoir, and height of the air-fluid interface above the dog. $P_H$ is positive for blood-access pressure greater than dialysate case pressure. FIG. 12(b) is a graph of $$\Sigma \frac{\Delta V_i}{P_H - P_{c,V_i}} \text{ vs } t$$

During inflow to dialyzer, two different slopes of this graph are found, indicating that different flow phenomena are occurring. Overall resistance is 0.18 mmHg/(ml/min) in the early phase and 1.1 in the later phase. Analysis of outflow indicates an initial outflow resistance of 0.55 mmHg/(ml/min), increasing to 2.0 mmHg/(ml/min), both of which are higher than inflow resistances. Photographic analysis of flow on the modified pyramidal support dialyzer has indicated that emptying does not follow the exact reverse steps of filling. Early in outflow, the ¼ inch nearest the center gasket "blanches," while the rest of the membrane package remains at full thickness. This may account for the higher resistance on outflow versus inflow.

The proportion of the overall resistance of the dialyzer which is due to the sorbent suspension flow may be estimated. During flow of the suspension through the test cell, the resistance was 0.07-0.21 mmHg/(ml/min), for one membrane package. For 15 membrane packages, the resistance would be, presumably 1/15 as much. Thus, the resistance to suspension flow is only approximately one percent of 1.1 mmHg/(ml/min) occurring during most of the inflow cycle for the entire device (above).

During long term operation of the dialyzer, the fill volumes decreased at most, 20%. Ultrafiltration could be determined by observation of the peak reservoir volume during each cycle. Ultrafiltration was generally found to be consistent with published ultrafiltration coefficient of Cuprophan PM150 (i.e., about one ml/(hr-mmHg-M$^2$). Residual volume (volume which could be removed from package at end of outflow period) was also constant, at about ten percent of fill volume.

Figure 13A:
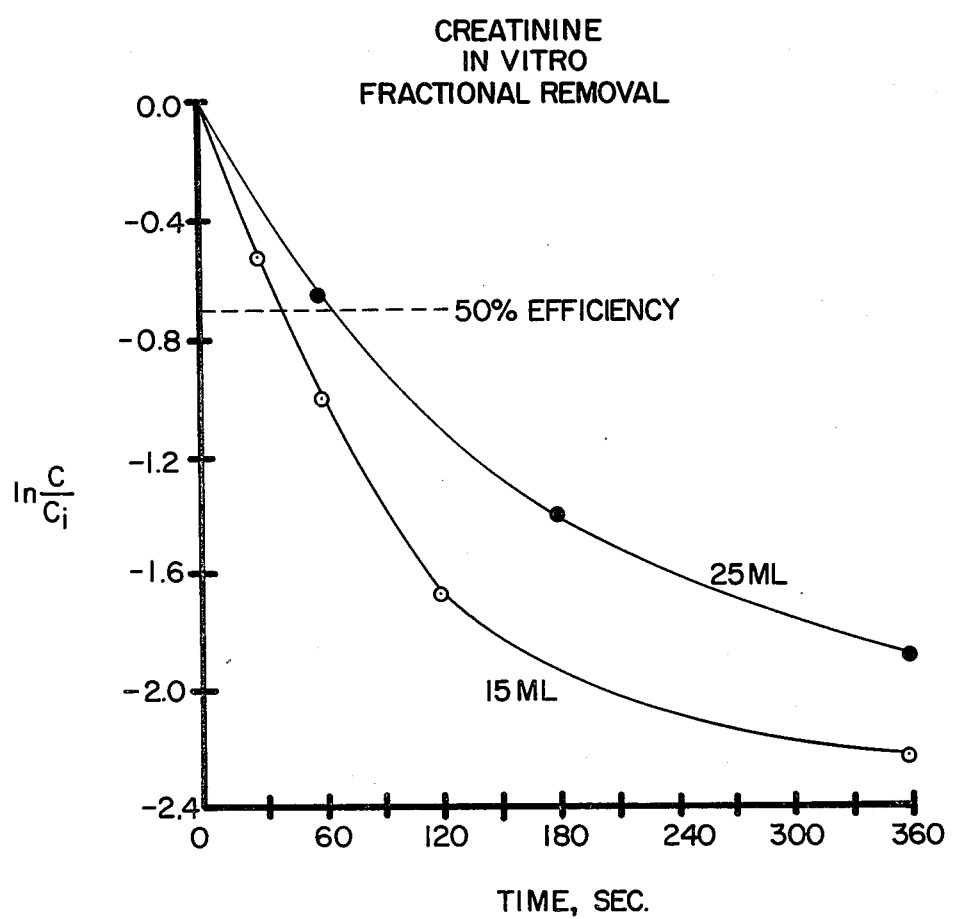
FIG. 13(a) is a graph of fluid volumes versus time showing creatinine inflow-outflow concentration changes for the dialyzer apparatus operated in a trapezoid mode.

Inflow-outflow concentration changes for creatinine were determined during in vitro tests at various flow modes, cycle times and volumes of fluid. Fluid volumes of 2.5 and 4.2 mls per package are shown in FIG. 13(a) for the dialyzer apparatus, operated at trapezoid mode. Fractional removal is relatively independent of fill volume, as evidenced by similar values of $K_o$. The saw-tooth mode had a slightly lower fractional removal, because the average residence time of fluid in the dialyzer was shorter. For either mode, the slope for $\ln(C/C_i)$ versus time varies with cycle time. As cycle time increases, the slope decreases. The mass transfer coefficient for the dialyzer is, therefore, dependent upon cycle time. An overall mass transfer coefficient can be determined for a cycle time yielding 50% efficiency (see above). The value of $K_{o,0.5}$ is $13.3 \times 10^{-3}$ cm/min for the trapezoid flow at a fill volume of 4.2 mls per membrane package, and $14.6 \times 10^{-3}$ for 2.5 mls/pkg. At the same fill volume, the $K_{o,0.5}$ for the saw-tooth flow is $8 \times 10^{-3}$. A cycle time of 60 seconds would be necessary for 50% creatinine removal with trapezoid flow at 4.2 fill volume per package. Clearance for such a dialyzer would thus be 50% of the blood treatment rate, or approximately 2.1 ml/min/membrane package. Since each membrane package has a total area of about 200 cm$^2$, this represents a creatinine clearance of 105 ml/min M$^2$.

Figure 13B:
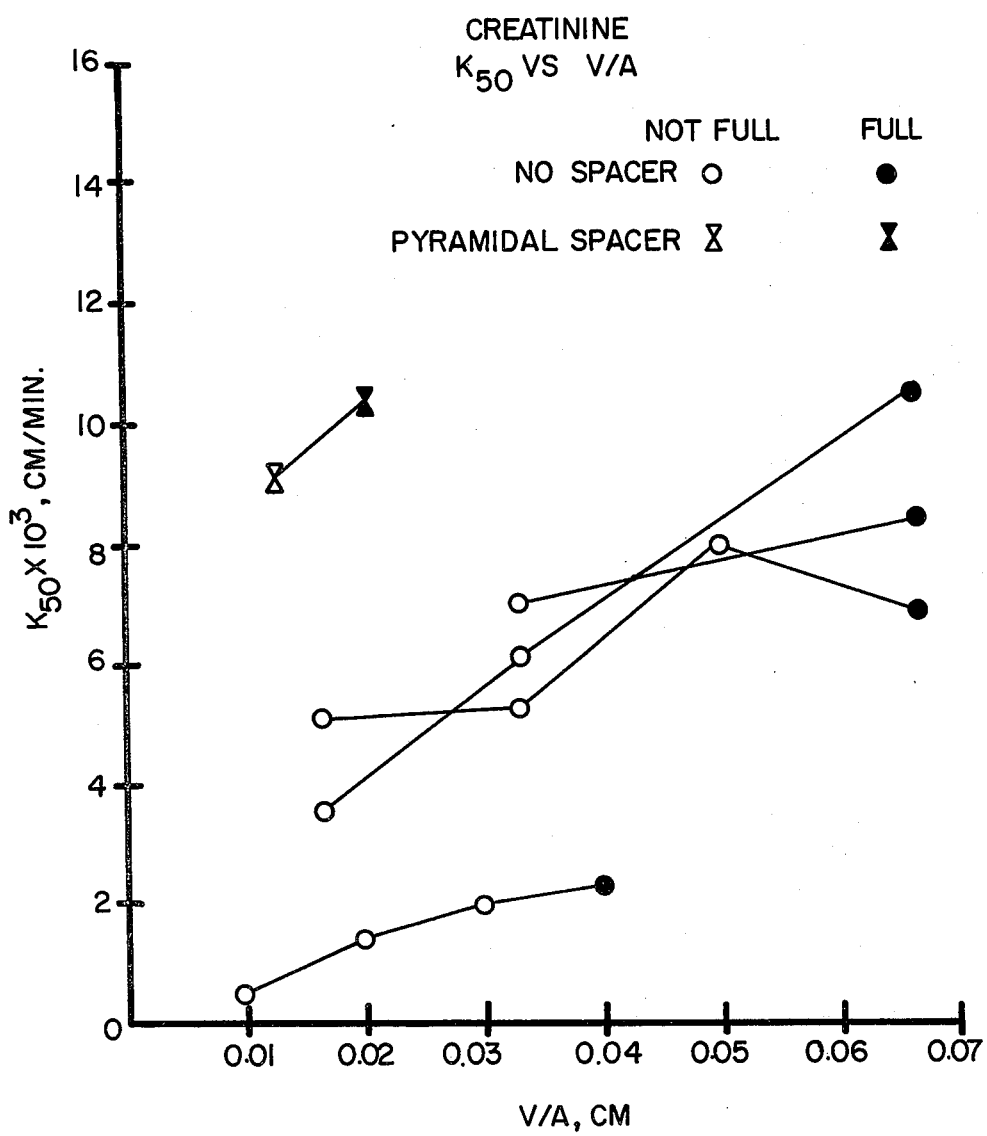
FIG. 13(b) shows mass transfer coefficients for dialyzer apparatus having no spacers and pyramid-type spacers as shown in this invention.

FIG. 13(b) shows the mass transfer coefficient for dialyzer apparatus for models with no membrane spacer and with a pyramid type spacer as shown in FIGS. 1 through 3, operated at saw-tooth mode. Results for a given dialyzer are shown for several volumes connected by a solid line. The maximum value of $V_f/A$ represents a "full" dialyzer, i.e., filled by syringe to about 300 mmHg. $K_o$ apparently increases with fill volume against theoretical prediction. This may be accounted for by a point-to-point variation in A, which could be a function of $V_f$ instead of constant as assumed in Equation 3. Although $K_o$ increases with $V_f$, operation at large $V_f/A$ is a disadvantage since an excessive fill volume and cycle time would be required to achieve clinically desirable clearances. FIG. 13(b) shows that dialyzers with no spacers are not as good as those with pyramidal spacers as shown in this invention, which resulted in much more uniform blood column thickness.

The dialyzer apparatus of this invention (using a modified pyramidal spacer) had the optional mass transfer coefficient ($10.3 \times 10^{-3}$, at saw-tooth operation), the best obtained of any dialyzer apparatus.

Figure 13C:
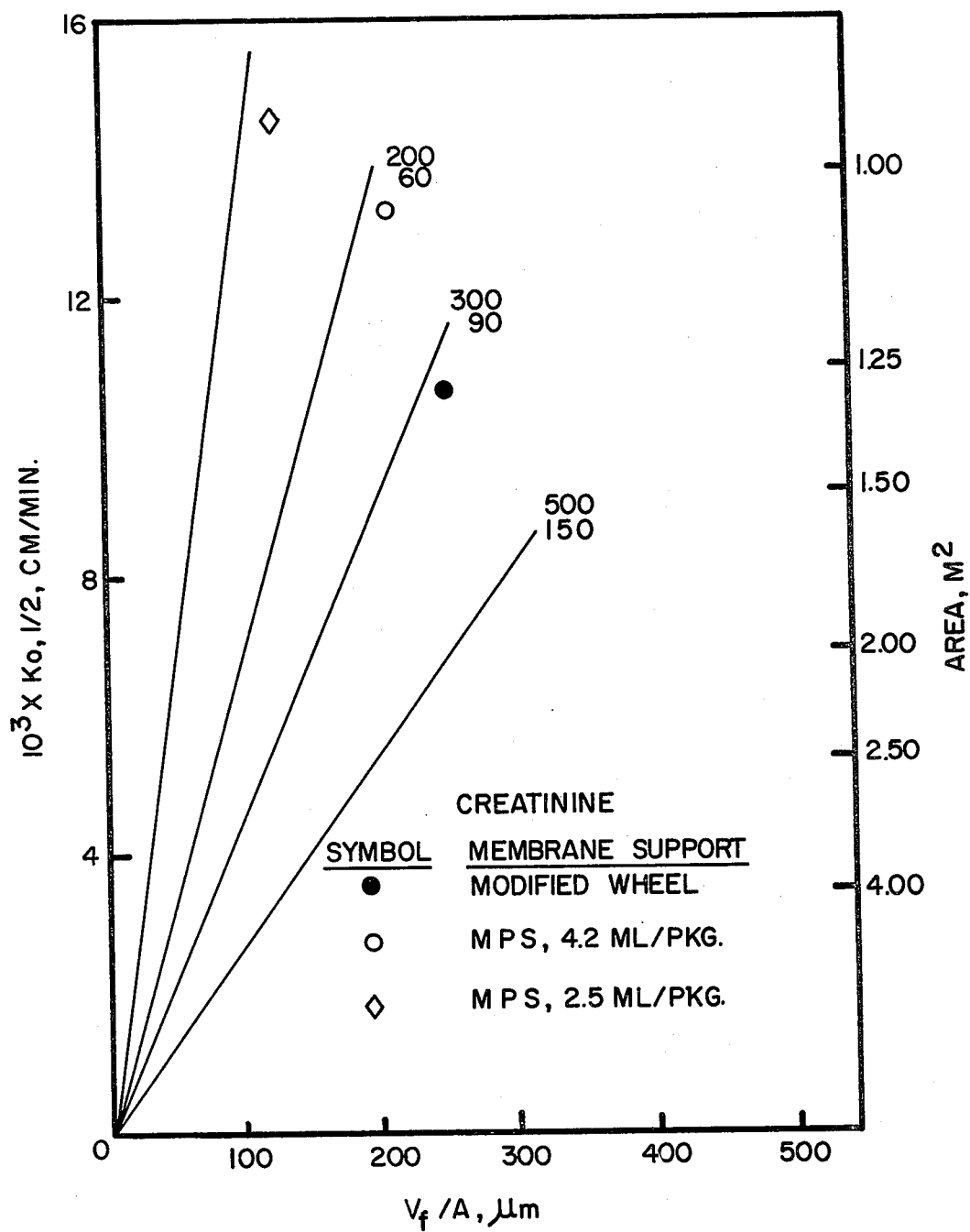
FIG. 13(C) shows creatinine removal for controlling dialyzer apparatus at various cycle times.

FIG. 13(c) contrasts different dialyzer apparatus designs, operating at trapezoid flow. Parametric lines are included representing $K_{o,0.5}$, versus $V_v/A$ for 200 ml/min blood flow at various $V_f$ to achieve 50% creatinine removal. Scaled-up dialyzer membrane area is shown on the right-hand ordinate, calculated using flow rate (200 ml/min), cycle time (to give 50% efficiency), and blood column thickness. The "best" dialyzer can be found by comparing the parametric lines. Most desirable is a combination of small A and small $V_f$. These criteria correspond to the higher-sloped lines, where the apparatus had a modified pyramidal spacer (MPS). For very thin blood column thicknesses, a small increase in $K_o$ greatly decreases the required fill volume, which is a significant clinical advantage. Simultaneously, the membrane area is reduced as $K_o$ increases, which results in advantages in cost and biocompatability.

Figure 14:
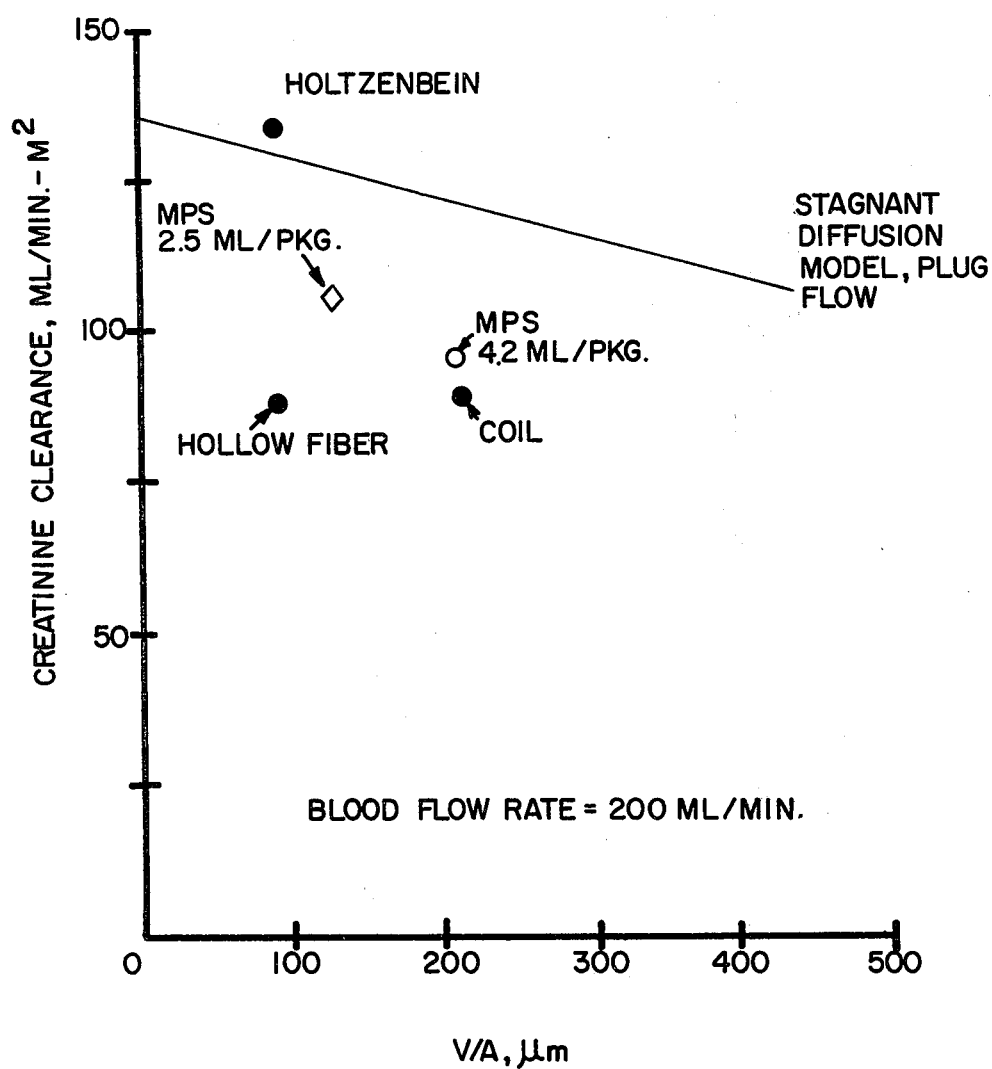
FIG. 14 depicts theoretical predicts of clearance for dialyzer apparatus of different blood film thickness.

A stagnant diffusion model of mass transfer reported elsewhere has been developed for both reciprocating and flow-through dialyzers. FIG. 14 depicts the theoretical predictions of clearance per M$^2$ surface area, for dialyzers of various blood film thickness, (2 $V_f/A$), at a blood treatment (or blood flow) rate of 200 ml/min. Included in FIG. 14 are representative in vitro clearances for hollow fiber, coil, and plate dialyzers currently in use. Clearance per surface area for stretched nylon and MPS dialyzers are obtained from the data of in vitro fractional removal tests at trapezoid modes. The clearances of standard flow-through dialyzers are, in general, slightly less than the clearances predicted by the stagnant diffusion model. The clearances of stretched nylon and MPS dialyzers at a trapezoid mode are also slightly less than predicted. At the blood treatment rate shown in FIG. 11, the clearances of reciprocating dialyzers at trapezoid modes are comparable to flow-through dialyzers of similar blood film thickness.

In vivo dialysis experiments were performed with modified pyramidal support dialyzers containing 13 to 60 membrane packages (0.3 to 1.2 M$^2$ surface area). Duration of dialysis was 150 to 240 minutes. During this time, volume changes in the dialyzer were recorded by measurement of the total effluent volume on sample cycles, or by measurement of changes in the reservoir volume, and subtracting the compliance of the case these volume changes. The fill volume of the dialyzer decreased only 10 to 20% during the entire 150 to 240 minute run. The suspension volume increased, due to ultrafiltration of fluids in the membranes, as described above. The initial suspension volume was one liter per 0.6 m² dialyzer.

During dialysis of the dog, body temperature, blood pressure, and general appearance did not change. Pulse varied from 60 to 90 according to the level of apparent apprehension of the dog. No clotting of the dialyzer occurred, so long as the activated clotting time of the animal was kept between 1.5 and two times of normal. Cycle time for these dialyzer tests was 60–72 seconds (48–54 seconds inflow, 12–18 outflow).

Figure 15A:
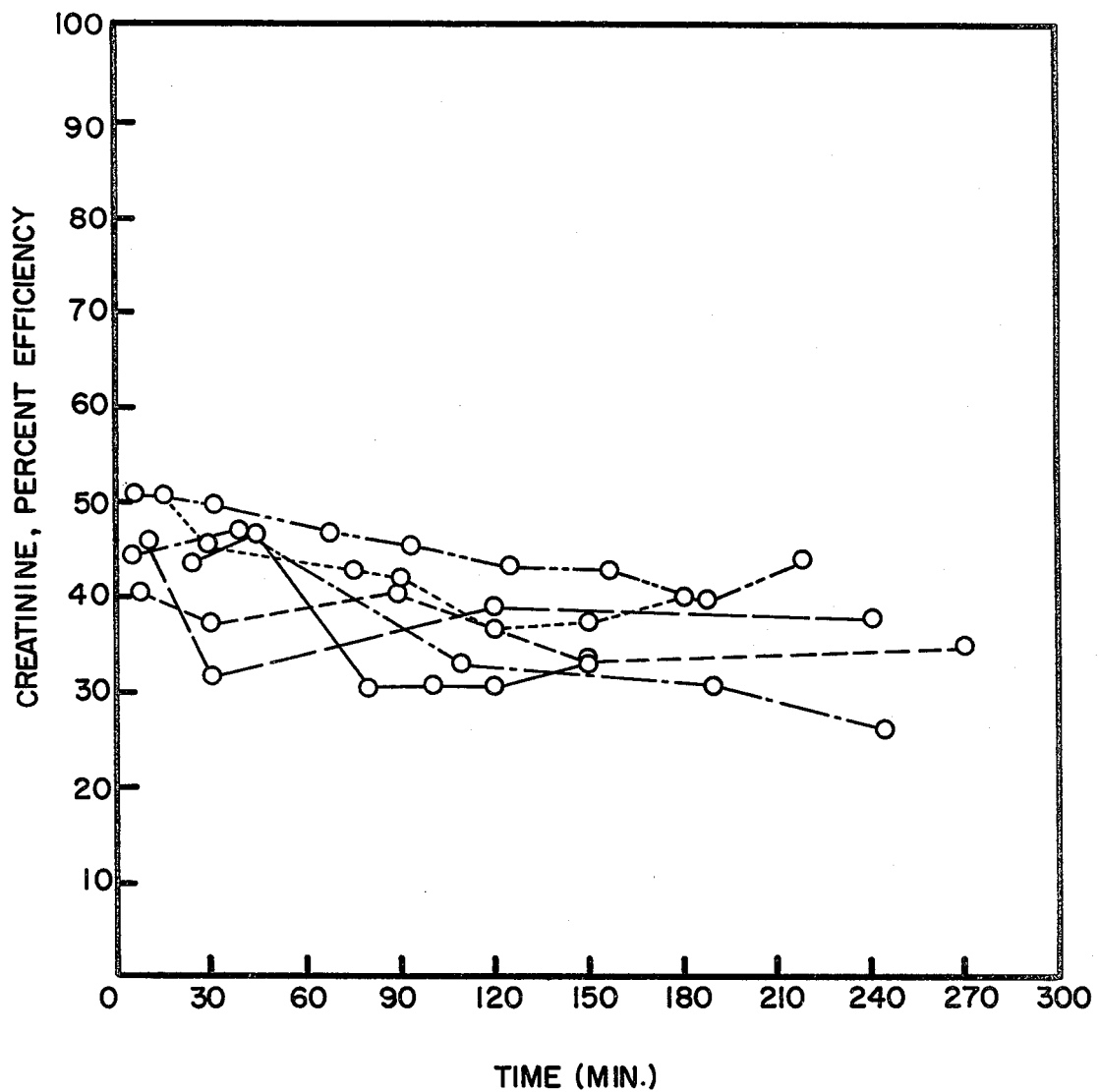
FIG. 15(a) is a graph of creatinine efficiency versus time for different dialyzer apparatus.

Inflow-outflow blood samples were analyzed for urea and creatinine. According to the fractional removal tests, a 40–60% efficiency would be expected for creatinine at the cycle times tested depending on whether the fill-volume versus time relationship was similar to the saw-tooth or trapezoid modes. FIG. 15(a) indicates that these efficiencies were achieved (approximately) for creatinine removal, for all dialyzers tested. Efficiency of creatinine removal decreased slightly with time during the first hour, but it remained relatively constant afterwards, indicating a lack of significant saturation of sorbents near the membranes.

Figure 15B:
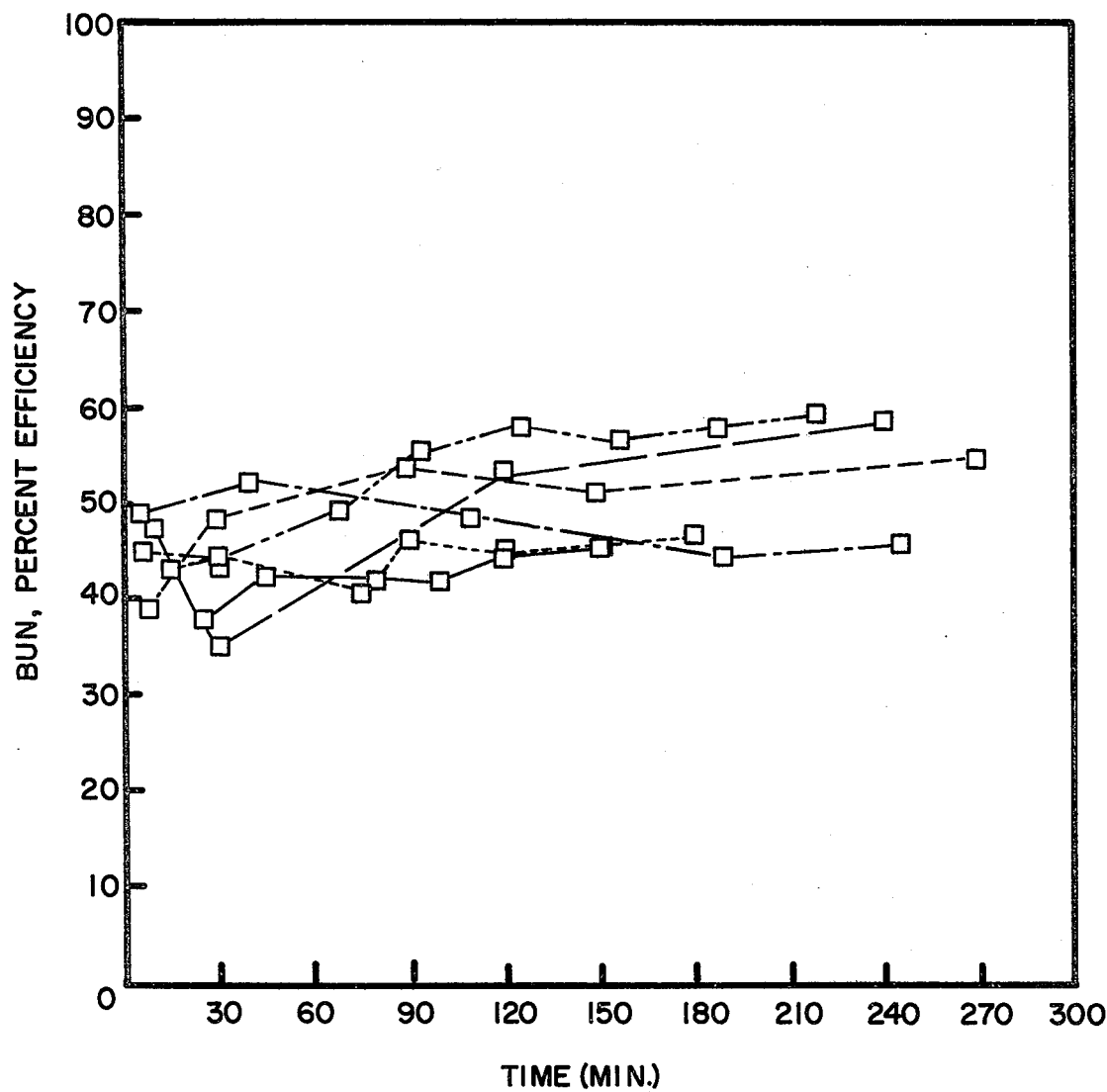
FIG. 15(b) is a graph of urea removal efficiency versus time for different dialyzer apparatus.

The efficiency of urea removal of the dialyzers averaged 35–60%, with some variation between dialyzers (FIG. 15(b)). No saturation or diminution of function was detected during three-four hours of dialysis. Given that the diffusivity of urea is higher than creatinine, the higher efficiency for urea removal is to be expected. Therefore, the rate of urea removal from the sorbent suspension is not apparently limited by the urea-hydrolysis step.

Figure 16:
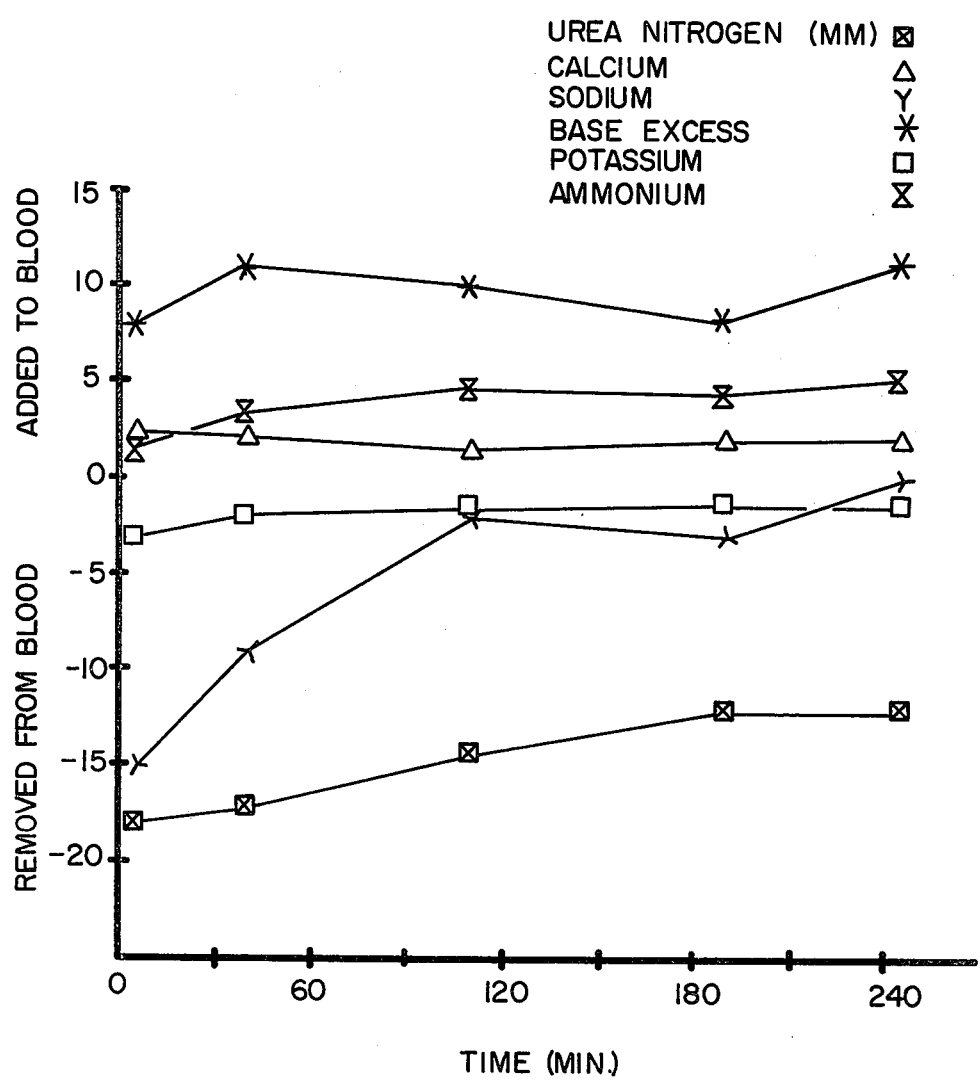
FIG. 16 illustrates changes in concentration of the elements in blood, during operation of the dialyzer with a calcium-sodium loaded zeolite.

For support of a uremic animal, it is necessary to have an appropriate ion balance during dialysis. Return of base and calcium to the blood is desirable. Moderate potassium and sodium removal is usually desirable. These goals are met by the calcium-sodium loaded zeolite W. FIG. 16 the change in concentration of calcium, base excess, potassium, ammonium, and sodium, for the duration of one dialyzer test (7/2/80, 60 membrane packages).

Figure 17:
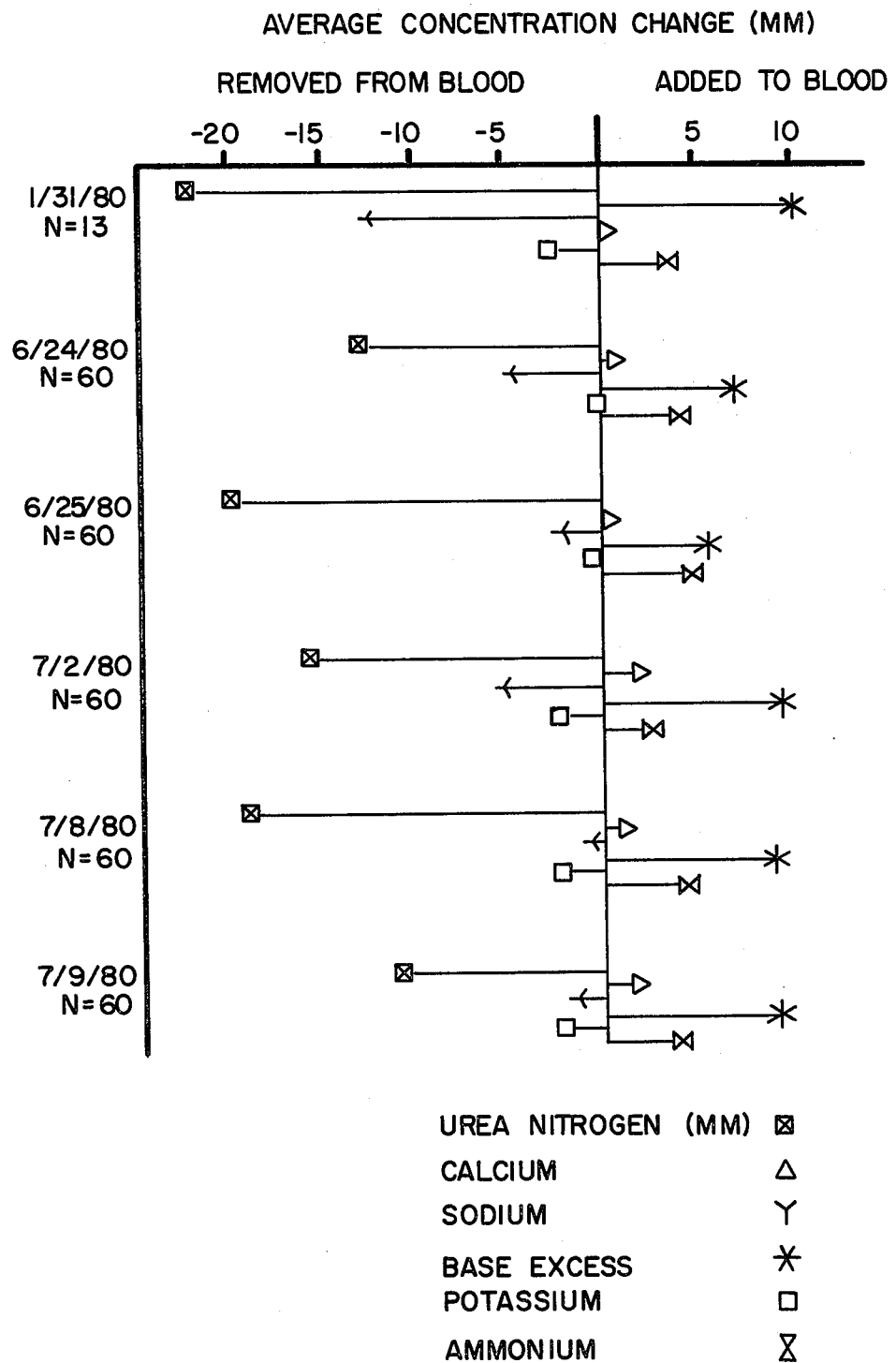
FIG. 17 illustrates changes in concentration for each in vivo test conducted.

It is seen that the concentration change for urea (mM urea N) is larger than any other concentration change. Bicarbonate is returned at a fairly constant 10 mEq/L concentration change throughout the dialysis. Sodium and potassium are both removed, more rapidly at the beginning than at the end of dialysis. Ammonium is returned in modest amount (up to 5 mEq/L) to the blood. Calcium return is modest also and diminishes during dialysis procedure. Overall, cation balance can be described as a large urea nitrogen, sodium, and potassium removal rate, with a small return of calcium and ammonium to the patient. These concentration changes during dialysis were reproducible during the six in vivo tests. The average inflow-outflow concentration change for each of the in vivo experiments is indicated in FIG. 17. In each experiment, urea nitrogen, sodium and potassium are removed, while modest addition of calcium and ammonium occurs to the blood. Bicarbonate return is somewhat dependent upon rate of urea removal, but is generally eight to ten mEq/L concentration change.

The sorbent suspension reciprocating dialyzer cannot function without some return of ammonium ions to the patient. In spite of the outflow concentration of ammonium reaching five mEq/L, inflow concentrations of ammonium to the dialyzer never goes above normal range. Thus, the animal's liver is able to metabolize the ammonia successfully during the dialysis procedure. The final outflow ammonium concentration is predictable from an equilibrium model, in which the ammonium flux into the dialyzer sorbent suspension is assumed to be equally mixed with all sorbent particles.

With respect to the screen type spacer element, this spacer has been shown to be able to handle denser slurry, over 500 g/L, have low resistance, high mass transfer, and provide a thin, uniform blood space. By providing melted outer rims and continuous melted center surfaces, sealing was enhanced. An outer rim of 0.02 inches permitted limited slurry flow. Caking was observed with 400 g/L of sorbents during a fractional test and a half hour pumping test with pressure/vacuum. No loss of "blood" movement was observed, however, during the pumping test. Mass transfer $(8 \times 10^{-3}$ cm/min) was achieved along with producing a thin blood column with the apparatus having moderate resistance.

Flow into and out of the dialyzer is limited by the membrane package compliance, and the rate of this flow is dependent on this resistance of the dialyzer and hydrostatic pressure head. The dialyzer apparatus may be operated for up to 240 minutes without significant loss in fill volume. During this time, two to three ml of sorbent suspension flows into and out of each membrane package suspension compartment. A small portion of overall resistance is related to sorbent suspension flow. In unidirectional flow, only about 50 ml of the same sorbent suspension will flow before marked increase in resistance occurs (time of flow proportional to $V^{(1.26-1.53)}$). The success of the sorbent suspension reciprocating dialyzer apparatus in maintaining the fluidity of the sorbents is felt to be due to:

1. the bi-directional flow of the sorbent suspension, allowing only a short time for aggregation of particles at any one location;
2. The continually changing relative position of the sorbent particles within the sorbent suspension due to deformation of membranes into the suspension compartment during the operation; and
3. Intermittent contact of the membrane packages with the membrane supports, repeatedly causing areas of high shear rate, between the pyramids and the membranes.

The resistance of the dialyzer is somewhat difficult to determine, due to the overlying importance of compliance in limiting flow. However, it does appear that the outflow resistance of the dialyzer is higher than inflow resistance. Long term operation of the dialyzer does not seem to alter its mechanical properties, and the dialyzer apparatus can be operated with a single blood access, at modest transmembrane pressures.

The chemical efficiency of the reciprocating sorbent suspension dialyzer is markedly improved by the spacers of this invention on the dialysate side which produces a thin, flat blood column and yields a mass transfer coefficient of ten to 13 (depending on whether it was operated at "sawtooth" or "trapezoid" flow pattern). This mass transfer coefficient is comparable to that of flow-through dialyzers with similar average blood column thickness. A creatinine clearance of 100 ml/min, with a blood flow rate of 200 ml/min. can be obtained with the apparatus of this invention with a dialyzer having about 1.4 $M^2$ surface area, operated at a 60 cycle with a 200 ml maximum fill volume. In addition, the sorbent suspension utilized in the animal tests yielded ion balance appropriate for patients in renal failure, and the calcium-sodium zeolite, in combination with urease, allowed urea nitrogen, Na, and K removal, and modest calcium return to the blood.

What is claimed is:

1. A reciprocating dialyzer apparatus, comprising:
   membrane means defining a wall between a first chamber for receiving a fluid to be treated and a second chamber for receiving treating solution with treatment occurring through said wall in the presence of a fluid to be treated and treating solution in contact with opposite sides of said wall;
   first and second conduit means for separately providing access for said fluid to be treated to said first chamber and access for said treating solution to said second chamber, said first conduit means being a single conduit for introducing and withdrawing fluid to be treated from said first chamber through said single conduit, and said second conduit means providing treating solution to said second chamber to allow free flow of said treating solution in said second chamber; and
   spacer means in said second chamber with said spacer means permitting substantially free flow of said treating solution at said wall, said spacer means having alternating first and second portions extending over at least a substantial portion of said spacer means with said first portions being engageable with said wall to limit movement thereof without creating a block in the other of said chambers and said second portions being recessed from said wall to permit access thereto so that said treatment can occur at said wall, said second portion including a relatively flat pad and said first portion including a plurality of closely spaced first and second groups of protuberances extending from said pad with said second group of protuberances extending from said pad a distance greater than said first group of protuberances but without creating a block in the other of said chambers.

2. The dialyzer apparatus of claim 1 wherein said fluid to be treated received in said first chamber is blood and said treating solution received in said second chamber is a peritoneal dialysis fluid.

3. The dialyzer apparatus of claim 2 wherein said spacer means is positioned within said second chamber to limit movement of said wall without blocking the flow of blood in said first chamber and thereby limit the maximum amount of blood to be treated that can be introduced into said first chamber.

4. The dialyzer apparatus of claim 1 wherein said membrane means includes a pair of membranes which form spaced walls defining said first chamber therebetween with said walls having said second chambers at the opposite sides, and wherein said spacer means include spacer elements in each of said second chambers to limit movement of said pair of membranes.

5. The dialyzer apparatus of claim 4 wherein said apparatus includes sealing portions for sealing said membranes at the central and peripheral portions so that said walls having said spacer means engageable therewith extend between said central and peripheral portions of said membranes.

6. The dialyzer apparatus of claim 1 wherein said first and second portions of said spacer means are configured so that said first portion has minimum engagement with said wall.

7. The dialyzer apparatus of claim 1 wherein said protuberances are uniformly spaced in a square array.

8. The dialyzer apparatus of claim 1 wherein said protuberances have wall-engaging top portions adapted for minimal wall contact.

9. The dialyzer apparatus of claim 8 wherein said protuberances have a pyramidal shape.

10. The dialyzer apparatus of claim 8 wherein said protuberances have a conical shape.

11. The dialyzer apparatus of claim 1 wherein said second group of protuberances are columns that are less closely spaced than said closely spaced protuberances.

12. A reciprocating dialyzer apparatus, said apparatus comprising:
    a pair of membranes defining a blood chamber therebetween, said membranes having a central opening therein;
    central access means at said central opening of said membranes for providing a central blood access for introduction of blood into and for withdrawal of blood from said blood chamber through said central blood access;
    a pair of spacer means positioned at opposite sides of said pair of membranes, said spacer means having a substantially flat central portion with a central aperture therein, a substantially flat peripheral portion with treating solution access means therein, and a middle portion having a plurality of closely spaced first protuberances with substantially adjoining bottom sections and membrane engageable top sections of reduced area with respect to said bottom sections, said first protuberances being of a height insufficient to block the flow of blood in said blood chamber and being one of a pyramidal shape and a conical shape, said middle portion also having a plurality of columns in a square array with said columns extending outwardly beyond said first protuberances but without blocking the flow of blood into said blood chamber; and
    means for introducing treating solution through said access means in said peripheral portions of said spacer means into the area between said middle portion of said spacer means and said membranes for contact of said treating solution with said membranes to effect blood treatment thereat.

13. The dialyzer apparatus of claim 12 wherein said access means in said peripheral portion of said spacer means includes a plurality of spaced notches in said peripheral portions, and wherein said middle portions of said spacer means includes aperture means adjacent to said notches in said peripheral portions of said spacer means.

14. A reciprocating dialyzer apparatus, said apparatus comprising:
    a pair of membranes defining a blood chamber therebetween, said membranes having a central opening therein and stress lines oriented normally with respect to one another;
    central access means at said central opening of said membranes for providing a central blood access for introduction of blood into and for withdrawal of blood from said blood chamber through said central blood access;

a pair of spacer means positioned at opposite sides of said pair of membranes, said spacer means having a substantially smooth central portion with a central aperture therein, a substantially flat peripheral portion with treating solution access means therein, and a middle portion of a screen construction, said screen having a membrane engageable edge section and groups of strands with the strands of each group being substantially parallel with respect to the other strands of said group and angularly oriented with respect to the strands of other groups with the parallel strands of one such group forming said membrane engageable edge section of said spacer means so that said membrane engageable strands of said screen are normally oriented with respect to the stress lines of the membrane that is engageable with said strands; and means for introducing treating solution through said access means in said peripheral portion of said spacer means into the area between said middle portion of said spacer means and said membranes for contact of said treating solution with said membranes to effect blood treatment thereat.

15. A spacer element for membrane means of a blood treatment unit that receives blood at one side of said membrane means and treating solution at the other side of said membrane means, said spacer element comprising:

a central portion having a central aperture therein;

a substantially flat peripheral portion having a plurality of notches therein; and a middle portion having a plurality of closely spaced protuberances having membrane means engageable areas that are smaller than the base areas of said protuberances so that treating solution introduced through said notches in said peripheral portion is not unduly impeded from membrane contact by said middle portion of said spacer element and so that blood flow is not blocked at said one side of said membrane means, and said middle portion also having a second group of protuberances extending beyond said first mentioned protuberances but without blocking the flow of blood at said one side of said membrane means.

16. The spacer element of claim 15 wherein said second group of protuberances are columns positioned in a square array.

17. The spacer element of claim 15 wherein said middle portion includes a plurality of apertures adjacent to said notches in said peripheral portion.

18. A spacer element for membrane means having stress lines, said membrane means being a part of a treatment unit that receives a fluid to be treated at one side of said membrane means and treating solution at the other side of said membrane means, said spacer element comprising:

a central portion having a central aperture therein;

a substantially flat peripheral portion having a plurality of notches therein; and a middle portion that is a screen having membrane engageable strands which are normally oriented with respect to said stress lines of said membrane means whereby treating solution introduced through said notches in said peripheral portion is not unduly impeded from membrane contact by said middle portion of said spacer element and so that blood flow is not blocked at said one side of said membrane.

19. The spacer element of claim 18 wherein said treatment unit is a dialyzer unit for treatment of blood with said blood being at said one side of said membrane means and a peritoneal dialysis fluid being at said other side of said membrane means.

* * * * *